United States Patent
Deem et al.

(10) Patent No.: US 8,110,196 B2
(45) Date of Patent: Feb. 7, 2012

(54) METHODS AND COMPOSITIONS FOR POLYTOPIC VACCINATION

(75) Inventors: Michael W. Deem, West University Place, TX (US); Jeong-Man Park, Seoul (KR); Hao Zhou, Houston, TX (US)

(73) Assignee: Polytopas LLC, West University Place, TX (US)

( * ) Notice: Subject to any disclaimer, the term of this patent is extended or adjusted under 35 U.S.C. 154(b) by 1118 days.

(21) Appl. No.: 11/118,917

(22) Filed: Apr. 29, 2005

(65) Prior Publication Data

US 2006/0246081 A1 Nov. 2, 2006

(51) Int. Cl.
 *A61K 39/12* (2006.01)
 *A61K 39/295* (2006.01)
 *A61K 45/00* (2006.01)
 *A61K 47/00* (2006.01)

(52) U.S. Cl. .................. 424/202.1; 424/1.17; 424/1.49; 424/1.57; 424/1.69; 424/130.1; 424/139.1; 424/159.1; 424/178.1; 424/184.1; 424/186.1; 424/193.1; 424/196.11; 424/204.1; 424/278.1

(58) Field of Classification Search .................. None
See application file for complete search history.

(56) References Cited

U.S. PATENT DOCUMENTS 6,576,757 B1 * 6/2003 Punnonen et al. ......... 536/23.72

OTHER PUBLICATIONS

Nagafuchi et al., (Reviews in Medical Virology. 1998. vol. 8:97-111).*
Gardiner et al., (Vaccine 24(2006):287-292; available online Aug. 8, 2005).*
Zoulek et al., (J. of Medical Virology. 1986. vol. 19(1): 55-61).*
Ambrosch et al., (Vaccine. 1992. vol. 10, Supplement 1. pp. S142-S145).*
Migasena et al., (Vaccine. 1995. vol. 13. No. 2. pp. 168-174).*
Ruben et al., (Bull. Wld. Hlth Org. 1973. vol. 48 pp. 175-181).*
MacGregor et al. ( 7th Conf. Retrovir. Oppor Infect. Jan. 30-Feb. 2, 2000. San Franc Calif.; 7:224 (abstract 796).*
Villen et al., (Vaccine 2004. vol. 22:3523-3529).*
Yamshchikov et al., (Int. J .Cancer. 2001. vol. 92:703-711).*
Okamoto et al., (1998. J. of General Virology. vol. 9:694-704).*
Bachman et al., 1997 "Functional Maturation of an Antiviral Cytotoxic T-Cell Response" J Virol 71:5764-5768.
Chotwiwalthanakun et al., 2001 "Production of potent polyvalent antivenom against three elapid venoms using a low dose, low volume, multi-site immunization protocol" Toxicon 39:1487-1494.

(Continued)

*Primary Examiner* — Albert Navarro
*Assistant Examiner* — Ja'Na Hines
(74) *Attorney, Agent, or Firm* — Cheryl H. Agris

(57) ABSTRACT

The present invention relates to therapeutic and prophylactic methods for treating or preventing an infectious disease in a subject by stimulating or enhancing an immune response against an infectious agent causing the disease. The methods comprise administering to the subject a plurality of compositions, each composition being administered to a different site of the subject, wherein each site is, or substantially drains to, an anatomically distinct lymph node, a group of lymph nodes, a nonencapsulated cluster of lymphoid tissue, or the spleen. Each composition comprises at least one antigenic molecule having one or more epitopes of the same infectious agent or a strain thereof. The antigenic molecules of each composition comprise in aggregate a set of epitopes distinct from that of any other composition that is administered to the subject.

22 Claims, 8 Drawing Sheets

OTHER PUBLICATIONS

Figure 1:
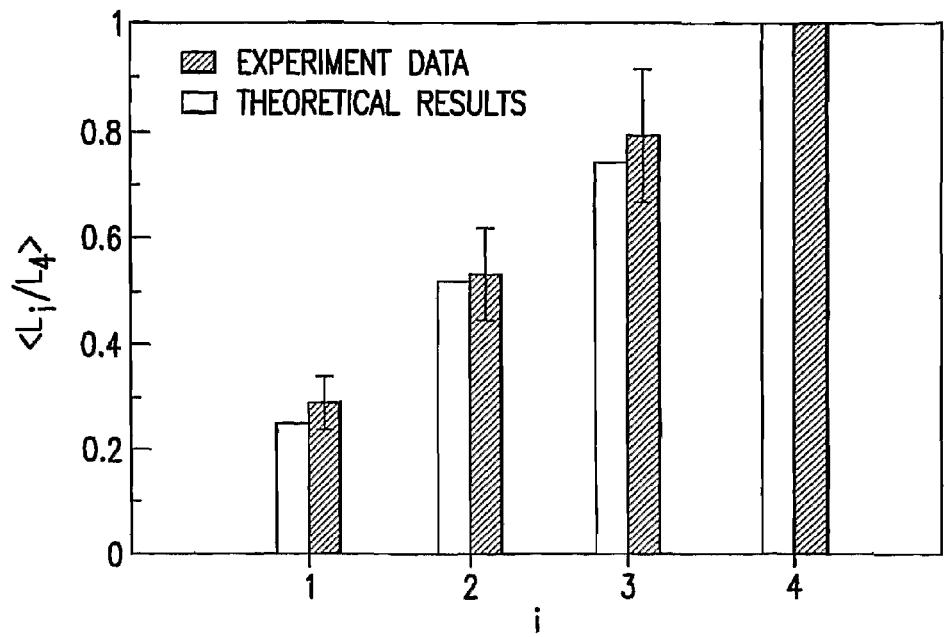

Huang et al., 2003 "Dengue 2 PDK-53 Virus as a Chimeric Carrier for Tetravalent Dengue Vaccine Development" J Virol 77:11436-11447.

Johnston and Davis 2004 "Future vaccines against emerging encephalitides" Arch Virol [Suppl] 18:207-220.

Klinman 2003 "CpG DNA as a vaccine adjuvant" Expert Rev Vaccine 2:305-315.

Rickinson and Moss 1997 "Human Cytotoxic T Lymphocyte Responses to Epstein-Barr Virus Infection" Annu Rev Immunol 15:405-431.

Sriprapat 2003 "The impact of a low dose, low volume, multi-site immunization on the production of therapeutic antivenoms in Thailand" Toxicon 41:57-64.

Vogel et al., A Compendium of Vaccine Adjuvants and Excipients (2nd Edition) http://www.niaid.nih.gov/hivvaccines/pdf/compendium.pdf (available Feb. 2002).

Air et al., "Location of antigenic sites on the three-dimensional structure of the influenza N2 virus neuraminidase," Virology 1985; 145(2):237-248

Anderson et al., "Overcoming original (antigenic) sin," Clin. Immunol.2001; 101(2):152-157.

Berry et al., "Analysis of the original antigenic sin response to the major outer membrane protein of Chlamydia trachomatis," J. Infect Dis. 1999; 179(1):180-186.

Bertoletti et al., "Cytotoxic T lymphocyte response to a wild type hepatitis B virus epitope in patients chronically infected by variant viruses carrying substitutions within the epitope," J. Exp. Med. 1994; 180(3):933-943.

Bertoletti et al., "Natural variants of cytotoxic epitopes are T-cell receptor antagonists for antiviral cytotoxic T cells," Nature 1994; 369(6479):407-410.

Brehm et al., "T cell immunodominance and maintenance of memory regulated by unexpectedly cross-reactive pathogens," Nat. Immunol. 2002; 3(7):627-634.

Busch et al., "MHC class I/peptide stability: implications for immunodominance, in vitro proliferation, and diversity of responding CTL," J. Immunol. 1998; 160(9):4441-4448.

Bush et al., "Positive selection on the H3 hemagglutinin gene of human influenza virus A," Mol. Biol. Evol. 1999; 16(11):1457-1465.

Choi et al., "High avidity antigen-specific CTL identified by CD8-independent tetramer staining," J. Immunol. 2003; 171(10):5116-5123.

Cole et al., "Efficient priming of CD8+ memory T cells specific for a subdominant epitope following Sendai virus infection," J. Immunol. 1997; 158(9):4301-4309

Cole et al., "Binding motifs predict major histocompatibility complex class II-restricted epitopes in the Sendai virus M protein," J. Virol. 1995; 69(12):8057-8060.

Corbet et al., "Optimization and immune recognition of multiple novel conserved HLA-A2, human immunodeficiency virus type 1-specific CTL epitopes," J. Gen. Virol 2003; 84:2409-2421.

Cox et al., "The molecular epidemiology of influenza virus," Sem. Virol. 1995; 6:359-370.

Deem, "Complexity in the immune system: New opportunities for chemical engineering research," Am. Institute Chem. Engineers J. 2004; 50(4):734-738.

Deem et al., "Sequence space localization in the immune system response to vaccination and disease," Phys. Rev. Lett. 2003; 91:68101-68104.

Duraiswamy et al., "Induction of therapeutic T-cell responses to subdominant tumor-associated viral oncogene after immunization with replication-incompetent polyepitope adenovirus vaccine," Cancer Res. 2004; 64(4):1483-1489.

Elliott et al., "Peptide based cytotoxic T-cell vaccines; delivery of multiple epitopes, help, memory and problems," Vaccine 1999; 17(15-16):2009-2019.

Fazekas de St. Groth and Webster, "Disquisitions of Original Antigenic Sin. I. Evidence in man." J Exp Med. Sep. 1, 1966; 124(3):331-45.

Good et al., "'Original antigenic sin', T cell memory, and malaria sporozoite immunity: an hypothesis for immune evasion," Parasite Immunol. 1993; 15(4):187-193.

Goulder et al., "Patterns of immunodominance in HIV-1-specific cytotoxic T lymphocyte responses in two human histocompatibility leukocyte antigens (HLA)-identical siblings with HLA-A *0201 are influenced by epitope mutations," J. Exp. Med. 1997; 185(8):1423-1433.

Gupta and Deem, "Quantifying influenza vaccine efficacy and antigenic distance," Quant. Biol., doc. No. 0503030 2005; 1-25.

Harcourt et al., "Evidence for lack of cross-genotype protection of CD4+ T cell responses during chronic hepatitis C virus infection," Clin. Exp. Immunol. 2003; 131(1):122-129.

Himoudi et al., "Comparative vaccine studies in HLA-A2.1-transgenic mice reveal a clustered organization of epitopes presented in hepatitis C virus natural infection," J. Virol. 2002; 76(24):12735-12746.

Hioe et al., "Overlapping cytotoxic T-lymphocyte and B-cell antigenic sites on the influenza virus H5 hemagglutinin," J. Virol. 1990; 64(12):6246-6251.

Hollsberg, "Contribution of HLA class I allele expression to CD8+ T-cell responses against Epstein-Barr virus," Scand. J. Immunol. 2002, 55(2):189-195.

Hon et al., "Tracking dendritic cells in vivo: insights into DC biology and function," Immunol. Res. 2004; 29(1-3):69-80.

Lichterfeld et al., "Immunodominance of HIV-1-specific CD8(+) T-cell responses in acute HIV-1 infection: at the crossroads of viral and host genetics," Trends Immunol. 2005; 26(3):166-171.

Makki et al., "Immunization against a dominant tumor antigen abrogates immunogenicity of the tumor," Cancer Immun. 2002; 2:4 (1-13).

Martin-Fontecha et al., "Regulation of dendritic cell migration to the draining lymph node: impact on T lymphocyte traffic and priming," J. Exp. Med. 2003; 198(4):615-621.

McKinney et al., "Recognition of variant HIV-1 epitopes from diverse viral subtypes by vaccine-induced CTL," J. Immunol. 2004; 173(3):1941-1950.

McLachlan et al., "Mast cell-derived tumor necrosis factor induces hypertrophy of draining lymph nodes during infection," Nat. Immunol. 2003; 4(12):1199-1205.

Meijers et al., "Crystal structures of murine MHC Class I H-2 D(b) and K(b) molecules in complex with CTL epitopes from influenza A virus: implications for TCR repertoire selection and immunodominance," J. Mol. Biol. 2005; 345(5):1099-1110.

Micheletti et al., "Selective amino acid substitutions of a subdominant Epstein-Barr virus LMP2-derived epitope increase HLA/peptide complex stability and immunogenicity: implications for immunotherapy of Epstein-Barr virus-associated malignancies," Eur. J. Immunol. 1999; 29(8):2579-2589

Mongkolsapaya et al., "Original antigenic sin and apoptosis in the pathogenesis of dengue hemorrhagic fever," Nat. Med. 2003; 9(7):921-927.

Munoz and Deem, "Epitope analysis for influenza vaccine design," Vaccine 2005; 23:1144-1148.

Oukka et al., "Protection against lethal viral infection by vaccination with nonimmunodominant peptides," J. Immunol. 1996; 157(7):3039-3045.

Park and Deem, "Correlations in the T-cell response to altered peptide ligands," Physica A. 2004; 341:455-470.

Pashine et al., "Targeting the innate immune response with improved vaccine adjuvants," Nat. Med. 2005; 11(4 Suppl):S63-S68.

Plotkin, "Vaccines: past, present and future," Nature Med. 2005; 11(4):S5-S11.

Regner et al., "Antiviral cytotoxic T cells cross-reactively recognize disparate peptide determinants from related viruses but ignore more similar self- and foreign determinants," J. Immunol. 2001; 166(6):3820-3828.

Robinson et al., "T cell vaccines for microbial infections," Nature Med. 2005; 11(4):S25-S32.

Roehrig, "Antigenic structure of flavivirus proteins," Adv. Virus Res. 2003; 59:141-175.

Rothman, "Immunology and immunopathogenesis of dengue disease," Adv. Virus Res. 2003; 60:397-419.

Rothman et al., "Induction of T lymphocyte responses to dengue virus by a candidate tetravalent live attenuated dengue virus vaccine," Vaccine 2001; 19(32):4694-4699.

Santra et al., "Recombinant canarypox vaccine-elicited CTL specific for dominant and subdominant simian Immunodeficiency virus epitopes in rhesus monkeys," *J. Immunol.* 2002; 168(4):1847-1853.

Savage et al., "Induction of viral and tumour specific CTL responses using antibody targeted HLA class I peptide complexes," *Br. J. Cancer* 2002;86(8):1336-1342.

Schreiber et al., "Immunodominance and tumor escape," *Semin. Cancer Biol.* 2002; 12(1):25-31.

Sette and Fikes, "Epitope-based vaccines: an update on epitope identification, vaccine design and delivery," *Curr. Opin. Immunol.* 2003; 15(4):461-470.

Tan et al., "Modulation of base-specific mutation and recommendation rates enables functional adaptation within the context of the genetic code," *J. Mol. Evol.* 2004; 59:385-399.

Taracha et al., "Parasite strain specificity of bovine cytotoxic T cell responses to *Theileria parva* is determined primarily by immunodominance," *J. Immunol.* 1995; 155(10):4854-4860.

Tulip et al., "Refined atomic structures of N9 subtype influenza virus neuraminidase and escape mutants,"*J. Mol. Biol* 1991; 221(2):487-497.

Turner et al., "Lack of prominent peptide-major histocompatibility complex features limits repertoire diversity in virus-specific CD8+ T cell populations," *Nature Immunology* 2005; 6(4):382-389.

Van der Most et al., "Analysis of cytotoxic T cell responses to dominant and subdominant epitopes during acute and chronic lymphocytic choriomeningitis virus infection," *J. Immunol*, 1996; 157(12):5543-5554.

Van Waes et al., "Immunodominance deters the response to other tumor antigens thereby favoring escape: prevention by vaccination with tumor variants selected with cloned cytolytic T cells in vitro," *Tissue Antigens* 1996; 47(5):399-407.

Yewdell and Del Val, "Immunodominance in TCD8+ responses to viruses: cell biology, cellular immunology, and mathematical models," *Immunity* 2004; 2:149-153.

Yewdell et al., "Immunodominance in major histocompatibility complex class I-restricted T lymphocyte responses," *Annu. Rev. Immunol.* 1999; 17:51-88.

\* cited by examiner

SEQUENCE LISTING

```
<160> NUMBER OF SEQ ID NOS: 110

<210> SEQ ID NO 1
<211> LENGTH: 18
<212> TYPE: PRT
<213> ORGANISM: Adenovirus

<400> SEQUENCE: 1

Tyr Leu Leu Glu Met Leu Trp Arg Leu Tyr Leu Gln Gln Asn Trp Trp
1               5                   10                  15

Thr Leu

<210> SEQ ID NO 2
<211> LENGTH: 18
<212> TYPE: PRT
<213> ORGANISM: Dengue
```

```
<400> SEQUENCE: 2

Thr Pro Glu Gly Ile Ile Pro Ala Leu Thr Pro Glu Gly Ile Ile Pro
1               5                   10                  15

Ser Met

<210> SEQ ID NO 3
<211> LENGTH: 18
<212> TYPE: PRT
<213> ORGANISM: Dengue

<400> SEQUENCE: 3

Thr Pro Glu Gly Ile Ile Pro Ala Leu Thr Pro Glu Gly Ile Ile Pro
1               5                   10                  15

Thr Leu

<210> SEQ ID NO 4
<211> LENGTH: 18
<212> TYPE: PRT
<213> ORGANISM: Epstein Barr virus

<400> SEQUENCE: 4

Cys Leu Ala Gly Leu Leu Thr Met Val Cys Leu Gly Gly Leu Leu Thr
1               5                   10                  15

Met Val

<210> SEQ ID NO 5
<211> LENGTH: 18
<212> TYPE: PRT
<213> ORGANISM: Epstein Barr virus

<400> SEQUENCE: 5

Gly Leu Cys Thr Leu Val Ala Met Leu Leu Leu Trp Thr Leu Val Val
1               5                   10                  15

Leu Leu

<210> SEQ ID NO 6
<211> LENGTH: 19
<212> TYPE: PRT
<213> ORGANISM: Epstein Barr virus

<400> SEQUENCE: 6

Ile Val Thr Asp Phe Ser Val Ile Lys Ala Val Phe Asp Arg Lys Ser
1               5                   10                  15

Asp Ala Lys

<210> SEQ ID NO 7
<211> LENGTH: 18
<212> TYPE: PRT
<213> ORGANISM: Epstein Barr virus

<400> SEQUENCE: 7

Gln Ala Lys Trp Arg Leu Gln Thr Leu Phe Leu Arg Gly Arg Ala Tyr
1               5                   10                  15

Gly Leu

<210> SEQ ID NO 8
<211> LENGTH: 18
<212> TYPE: PRT
<213> ORGANISM: Epstein Barr virus

<400> SEQUENCE: 8
```

```
Tyr Leu Ala Gly Leu Leu Thr Met Val Cys Leu Gly Gly Leu Leu Thr
1               5                   10                  15

Met Val

<210> SEQ ID NO 9
<211> LENGTH: 16
<212> TYPE: PRT
<213> ORGANISM: Flaviviridae

<400> SEQUENCE: 9

Glu Glu His Ser Gly Asn Glu Ile Arg Glu His Arg Lys Val Ala Ile
1               5                   10                  15

<210> SEQ ID NO 10
<211> LENGTH: 16
<212> TYPE: PRT
<213> ORGANISM: Flaviviridae

<400> SEQUENCE: 10

Glu Glu His Ser Gly Asn Glu Ile Thr Glu His Ser Gly Asn Glu Ile
1               5                   10                  15

<210> SEQ ID NO 11
<211> LENGTH: 16
<212> TYPE: PRT
<213> ORGANISM: Flaviviridae

<400> SEQUENCE: 11

Glu Glu His Ser Gly Asn Glu Ile Ala Glu His Thr Gly Arg Glu Ile
1               5                   10                  15

<210> SEQ ID NO 12
<211> LENGTH: 16
<212> TYPE: PRT
<213> ORGANISM: Flaviviridae

<400> SEQUENCE: 12

Glu Glu His Ser Gly Asn Glu Ile Glu Glu His Asp Gly Asn Glu Ile
1               5                   10                  15

<210> SEQ ID NO 13
<211> LENGTH: 20
<212> TYPE: PRT
<213> ORGANISM: Hepatitis B virus

<400> SEQUENCE: 13

Phe Leu Pro Ser Asp Phe Phe Pro Ser Val Phe Leu Pro Asn Asp Phe
1               5                   10                  15

Phe Pro Ser Val
                20

<210> SEQ ID NO 14
<211> LENGTH: 20
<212> TYPE: PRT
<213> ORGANISM: Hepatitis B virus

<400> SEQUENCE: 14

Phe Leu Pro Ser Asp Phe Phe Pro Ser Val Phe Leu Pro Asn Asp Phe
1               5                   10                  15

Phe Pro Ser Ala
                20

<210> SEQ ID NO 15
```

```
<211> LENGTH: 20
<212> TYPE: PRT
<213> ORGANISM: Hepatitis B virus

<400> SEQUENCE: 15

Phe Leu Pro Ser Asp Phe Phe Pro Ser Val Phe Leu Pro Val Asp Phe
1               5                   10                  15

Phe Pro Ser Val
            20

<210> SEQ ID NO 16
<211> LENGTH: 20
<212> TYPE: PRT
<213> ORGANISM: Hepatitis B virus

<400> SEQUENCE: 16

Phe Leu Pro Ser Asp Phe Phe Pro Ser Val Phe Leu Pro Ala Asp Phe
1               5                   10                  15

Phe Pro Ser Val
            20

<210> SEQ ID NO 17
<211> LENGTH: 20
<212> TYPE: PRT
<213> ORGANISM: Hepatitis B virus

<400> SEQUENCE: 17

Phe Leu Pro Ser Asp Phe Phe Pro Ser Val Phe Leu Pro Ala Asp Phe
1               5                   10                  15

Phe Pro Ser Ile
            20

<210> SEQ ID NO 18
<211> LENGTH: 18
<212> TYPE: PRT
<213> ORGANISM: Hepatitis C virus

<400> SEQUENCE: 18

Asp Leu Met Gly Tyr Ile Pro Leu Val Ile Leu Asp Ser Phe Asp Pro
1               5                   10                  15

Leu Arg

<210> SEQ ID NO 19
<211> LENGTH: 18
<212> TYPE: PRT
<213> ORGANISM: HIV

<400> SEQUENCE: 19

Gly Leu Ala Asp Gln Leu Ile His Leu Gly Leu Ala Asp Gln Leu Ile
1               5                   10                  15

His Met

<210> SEQ ID NO 20
<211> LENGTH: 18
<212> TYPE: PRT
<213> ORGANISM: HIV

<400> SEQUENCE: 20

Asn Val Trp Ala Thr His Ala Cys Tyr Asn Ile Trp Ala Thr His Ala
1               5                   10                  15

Cys Val
```

```
<210> SEQ ID NO 21
<211> LENGTH: 18
<212> TYPE: PRT
<213> ORGANISM: HIV

<400> SEQUENCE: 21

Arg Leu Arg Pro Gly Gly Lys Lys Lys Arg Leu Arg Pro Gly Gly Lys
1               5                   10                  15

Lys Cys

<210> SEQ ID NO 22
<211> LENGTH: 18
<212> TYPE: PRT
<213> ORGANISM: HIV

<400> SEQUENCE: 22

Ser Leu Val Lys His His Met Tyr Val Ser Leu Val Lys His His Met
1               5                   10                  15

Tyr Ile

<210> SEQ ID NO 23
<211> LENGTH: 18
<212> TYPE: PRT
<213> ORGANISM: HIV

<400> SEQUENCE: 23

Ser Leu Tyr Asn Thr Val Ala Thr Leu Ser Leu Phe Asn Thr Val Ala
1               5                   10                  15

Thr Leu

<210> SEQ ID NO 24
<211> LENGTH: 19
<212> TYPE: PRT
<213> ORGANISM: Influenza A

<400> SEQUENCE: 24

Ala Ser Asn Glu Asn Met Glu Thr Met Ser Ser Leu Glu Asn Phe Arg
1               5                   10                  15

Ala Tyr Val

<210> SEQ ID NO 25
<211> LENGTH: 18
<212> TYPE: PRT
<213> ORGANISM: Influenza A/PR8/34

<400> SEQUENCE: 25

Ala Ser Asn Glu Asn Met Glu Thr Met Ala Ser Asn Glu Asn Met Asp
1               5                   10                  15

Ala Met

<210> SEQ ID NO 26
<211> LENGTH: 18
<212> TYPE: PRT
<213> ORGANISM: Listeria

<400> SEQUENCE: 26

Gly Tyr Lys Asp Gly Asn Glu Tyr Ile Gly Tyr Leu Thr Asp Asn Asp
1               5                   10                  15

Glu Ile

<210> SEQ ID NO 27
<211> LENGTH: 18
```

```
<212> TYPE: PRT
<213> ORGANISM: Listeria

<400> SEQUENCE: 27

Lys Tyr Gly Val Ser Val Gln Asp Ile Ile Tyr Val Gly Asn Gly Gln
 1               5                  10                  15

Met Ile

<210> SEQ ID NO 28
<211> LENGTH: 18
<212> TYPE: PRT
<213> ORGANISM: Simian Immunodeficiency virus

<400> SEQUENCE: 28

Cys Thr Pro Tyr Asp Ile Asn Gln Met Ser Thr Pro Pro Leu Val Arg
 1               5                  10                  15

Leu Val

<210> SEQ ID NO 29
<211> LENGTH: 9
<212> TYPE: PRT
<213> ORGANISM: Influenza A

<400> SEQUENCE: 29

Thr Tyr Gln Arg Thr Arg Ala Leu Val
 1               5

<210> SEQ ID NO 30
<211> LENGTH: 9
<212> TYPE: PRT
<213> ORGANISM: Plasmodium Berghei

<400> SEQUENCE: 30

Ser Tyr Ile Pro Ser Ala Glu Lys Ile
 1               5

<210> SEQ ID NO 31
<211> LENGTH: 9
<212> TYPE: PRT
<213> ORGANISM: Murine cytomegalovirus

<400> SEQUENCE: 31

Tyr Pro His Phe Met Pro Thr Asn Leu
 1               5

<210> SEQ ID NO 32
<211> LENGTH: 9
<212> TYPE: PRT
<213> ORGANISM: Lymphocytic choriomeningitis virus

<400> SEQUENCE: 32

Arg Pro Gln Ala Ser Gly Val Tyr Met
 1               5

<210> SEQ ID NO 33
<211> LENGTH: 8
<212> TYPE: PRT
<213> ORGANISM: Influenza A

<400> SEQUENCE: 33

Ser Asp Tyr Glu Gly Arg Leu Ile
 1               5

<210> SEQ ID NO 34
```

```
<211> LENGTH: 9
<212> TYPE: PRT
<213> ORGANISM: Influenza A

<400> SEQUENCE: 34

Glu Glu Gly Ala Ile Val Gly Glu Ile
1               5

<210> SEQ ID NO 35
<211> LENGTH: 9
<212> TYPE: PRT
<213> ORGANISM: Influenza A

<400> SEQUENCE: 35

Ala Ser Asn Glu Asn Met Asp Ala Met
1               5

<210> SEQ ID NO 36
<211> LENGTH: 10
<212> TYPE: PRT
<213> ORGANISM: Adenovirus-5

<400> SEQUENCE: 36

Ser Gly Pro Ser Asn Thr Pro Pro Glu Ile
1               5                   10

<210> SEQ ID NO 37
<211> LENGTH: 8
<212> TYPE: PRT
<213> ORGANISM: Chicken ovalbumin

<400> SEQUENCE: 37

Ser Ile Ile Asn Phe Glu Lys Leu
1               5

<210> SEQ ID NO 38
<211> LENGTH: 9
<212> TYPE: PRT
<213> ORGANISM: Sendai virus

<400> SEQUENCE: 38

Phe Ala Pro Gly Asn Tyr Pro Ala Leu
1               5

<210> SEQ ID NO 39
<211> LENGTH: 9
<212> TYPE: PRT
<213> ORGANISM: Dengue

<400> SEQUENCE: 39

Thr Pro Glu Gly Ile Ile Pro Ala Leu
1               5

<210> SEQ ID NO 40
<211> LENGTH: 9
<212> TYPE: PRT
<213> ORGANISM: Dengue

<400> SEQUENCE: 40

Thr Pro Glu Gly Ile Ile Pro Ser Met
1               5

<210> SEQ ID NO 41
<211> LENGTH: 9
<212> TYPE: PRT
<213> ORGANISM: Dengue
```

```
<400> SEQUENCE: 41

Thr Pro Glu Gly Ile Ile Pro Thr Leu
 1               5

<210> SEQ ID NO 42
<211> LENGTH: 11
<212> TYPE: PRT
<213> ORGANISM: Dengue

<400> SEQUENCE: 42

Gly Thr Ser Gly Ser Pro Ile Ile Asp Lys Lys
 1               5                  10

<210> SEQ ID NO 43
<211> LENGTH: 11
<212> TYPE: PRT
<213> ORGANISM: Dengue

<400> SEQUENCE: 43

Gly Thr Ser Gly Ser Pro Ile Val Asp Arg Lys
 1               5                  10

<210> SEQ ID NO 44
<211> LENGTH: 11
<212> TYPE: PRT
<213> ORGANISM: Dengue

<400> SEQUENCE: 44

Gly Thr Ser Gly Ser Pro Ile Val Asp Lys Lys
 1               5                  10

<210> SEQ ID NO 45
<211> LENGTH: 11
<212> TYPE: PRT
<213> ORGANISM: Dengue

<400> SEQUENCE: 45

Gly Thr Ser Gly Ser Pro Ile Ala Asp Lys Lys
 1               5                  10

<210> SEQ ID NO 46
<211> LENGTH: 11
<212> TYPE: PRT
<213> ORGANISM: Dengue

<400> SEQUENCE: 46

Gly Thr Ser Gly Ser Pro Ile Val Asn Arg Glu
 1               5                  10

<210> SEQ ID NO 47
<211> LENGTH: 11
<212> TYPE: PRT
<213> ORGANISM: Dengue

<400> SEQUENCE: 47

Gly Thr Ser Gly Ser Pro Ile Ile Asn Arg Glu
 1               5                  10

<210> SEQ ID NO 48
<211> LENGTH: 11
<212> TYPE: PRT
<213> ORGANISM: Dengue

<400> SEQUENCE: 48
```

```
Gly Thr Ser Gly Ser Pro Ile Ile Asn Arg Lys
1               5                   10
```

<210> SEQ ID NO 49
<211> LENGTH: 12
<212> TYPE: PRT
<213> ORGANISM: Dengue

<400> SEQUENCE: 49

```
Leu Ala Pro Thr Arg Val Val Ala Ala Glu Met Glu
1               5                   10
```

<210> SEQ ID NO 50
<211> LENGTH: 12
<212> TYPE: PRT
<213> ORGANISM: Dengue

<400> SEQUENCE: 50

```
Leu Ala Pro Thr Arg Val Val Ala Ser Glu Met Ala
1               5                   10
```

<210> SEQ ID NO 51
<211> LENGTH: 15
<212> TYPE: PRT
<213> ORGANISM: Dengue

<400> SEQUENCE: 51

```
Asp Ser Gly Cys Val Val Ser Trp Lys Asn Lys Glu Leu Lys Cys
1               5                   10                  15
```

<210> SEQ ID NO 52
<211> LENGTH: 14
<212> TYPE: PRT
<213> ORGANISM: Dengue

<400> SEQUENCE: 52

```
Asp Ser Gly Val Ile Asn Trp Lys Gly Arg Glu Leu Lys Cys
1               5                   10
```

<210> SEQ ID NO 53
<211> LENGTH: 15
<212> TYPE: PRT
<213> ORGANISM: Dengue

<400> SEQUENCE: 53

```
Asp Met Gly Cys Val Ile Asn Trp Lys Gly Lys Glu Leu Lys Cys
1               5                   10                  15
```

<210> SEQ ID NO 54
<211> LENGTH: 15
<212> TYPE: PRT
<213> ORGANISM: Dengue

<400> SEQUENCE: 54

```
Asp Met Gly Cys Val Val Ser Trp Ser Gly Lys Glu Leu Lys Cys
1               5                   10                  15
```

<210> SEQ ID NO 55
<211> LENGTH: 9
<212> TYPE: PRT
<213> ORGANISM: Dengue

<400> SEQUENCE: 55

```
Gly Tyr Ile Ser Thr Arg Val Glu Met
1               5
```

```
<210> SEQ ID NO 56
<211> LENGTH: 9
<212> TYPE: PRT
<213> ORGANISM: Dengue

<400> SEQUENCE: 56

Gly Tyr Ile Ser Thr Arg Val Gly Met
1               5

<210> SEQ ID NO 57
<211> LENGTH: 9
<212> TYPE: PRT
<213> ORGANISM: Kunji

<400> SEQUENCE: 57

Gly Tyr Ile Ser Thr Arg Val Glu Leu
1               5

<210> SEQ ID NO 58
<211> LENGTH: 9
<212> TYPE: PRT
<213> ORGANISM: Murray Valley Encephalitis

<400> SEQUENCE: 58

Gly Tyr Ile Ala Thr Arg Val Glu Ala
1               5

<210> SEQ ID NO 59
<211> LENGTH: 9
<212> TYPE: PRT
<213> ORGANISM: West Nile Virus

<400> SEQUENCE: 59

Gly Tyr Ile Ala Thr Lys Val Glu Leu
1               5

<210> SEQ ID NO 60
<211> LENGTH: 9
<212> TYPE: PRT
<213> ORGANISM: Japanese Encephalitis

<400> SEQUENCE: 60

Gly Tyr Ile Ala Thr Lys Val Glu Leu
1               5

<210> SEQ ID NO 61
<211> LENGTH: 9
<212> TYPE: PRT
<213> ORGANISM: Yellow Fever

<400> SEQUENCE: 61

Gly Trp Ala Ala His Arg Ala Arg Ala
1               5

<210> SEQ ID NO 62
<211> LENGTH: 9
<212> TYPE: PRT
<213> ORGANISM: HIV

<400> SEQUENCE: 62

Gly Leu Ala Asp Gln Leu Ile His Leu
1               5

<210> SEQ ID NO 63
<211> LENGTH: 9
```

```
<212> TYPE: PRT
<213> ORGANISM: HIV

<400> SEQUENCE: 63

Gly Leu Ala Asp Gln Leu Ile His Met
1               5

<210> SEQ ID NO 64
<211> LENGTH: 9
<212> TYPE: PRT
<213> ORGANISM: HIV

<400> SEQUENCE: 64

Ser Leu Val Lys His His Met Tyr Val
1               5

<210> SEQ ID NO 65
<211> LENGTH: 9
<212> TYPE: PRT
<213> ORGANISM: HIV

<400> SEQUENCE: 65

Ser Leu Val Lys His His Met Tyr Ile
1               5

<210> SEQ ID NO 66
<211> LENGTH: 9
<212> TYPE: PRT
<213> ORGANISM: HIV

<400> SEQUENCE: 66

Asn Val Trp Ala Thr His Ala Cys Val
1               5

<210> SEQ ID NO 67
<211> LENGTH: 9
<212> TYPE: PRT
<213> ORGANISM: HIV

<400> SEQUENCE: 67

Asn Ile Trp Ala Thr His Ala Cys Val
1               5

<210> SEQ ID NO 68
<211> LENGTH: 9
<212> TYPE: PRT
<213> ORGANISM: HIV

<400> SEQUENCE: 68

Ser Leu Tyr Asn Thr Val Ala Thr Leu
1               5

<210> SEQ ID NO 69
<211> LENGTH: 9
<212> TYPE: PRT
<213> ORGANISM: HIV

<400> SEQUENCE: 69

Ser Leu Phe Asn Thr Val Ala Thr Leu
1               5

<210> SEQ ID NO 70
<211> LENGTH: 9
<212> TYPE: PRT
<213> ORGANISM: HIV
```

```
<400> SEQUENCE: 70

Arg Leu Arg Pro Gly Gly Lys Lys Lys
1               5

<210> SEQ ID NO 71
<211> LENGTH: 9
<212> TYPE: PRT
<213> ORGANISM: HIV

<400> SEQUENCE: 71

Arg Leu Arg Pro Gly Gly Lys Lys Cys
1               5

<210> SEQ ID NO 72
<211> LENGTH: 9
<212> TYPE: PRT
<213> ORGANISM: HIV-2

<400> SEQUENCE: 72

Thr Pro Tyr Asp Ile Asn Gln Met Leu
1               5

<210> SEQ ID NO 73
<211> LENGTH: 9
<212> TYPE: PRT
<213> ORGANISM: HIV-1

<400> SEQUENCE: 73

Thr Pro Gln Asp Leu Asn Met Met Leu
1               5

<210> SEQ ID NO 74
<211> LENGTH: 10
<212> TYPE: PRT
<213> ORGANISM: HIV-2

<400> SEQUENCE: 74

Thr Ser Thr Val Glu Glu Gln Ile Gln Trp
1               5                   10

<210> SEQ ID NO 75
<211> LENGTH: 10
<212> TYPE: PRT
<213> ORGANISM: HIV-1

<400> SEQUENCE: 75

Thr Ser Thr Leu Gln Glu Gln Ile Gly Trp
1               5                   10

<210> SEQ ID NO 76
<211> LENGTH: 9
<212> TYPE: PRT
<213> ORGANISM: HIV-1

<400> SEQUENCE: 76

Ala Leu Thr Asp Ile Cys Thr Glu Met
1               5

<210> SEQ ID NO 77
<211> LENGTH: 9
<212> TYPE: PRT
<213> ORGANISM: HIV-1

<400> SEQUENCE: 77

Ala Leu Val Glu Ile Cys Thr Glu Met
```

```
<210> SEQ ID NO 78
<211> LENGTH: 9
<212> TYPE: PRT
<213> ORGANISM: HIV-1

<400> SEQUENCE: 78

Ala Leu Thr Ala Ile Cys Glu Glu Met
1               5

<210> SEQ ID NO 79
<211> LENGTH: 9
<212> TYPE: PRT
<213> ORGANISM: HIV-1

<400> SEQUENCE: 79

Ala Leu Ile Glu Ile Cys Ser Glu Met
1               5

<210> SEQ ID NO 80
<211> LENGTH: 10
<212> TYPE: PRT
<213> ORGANISM: HIV-1

<400> SEQUENCE: 80

Lys Met Ile Gly Gly Ile Gly Gly Phe Ile
1               5                   10

<210> SEQ ID NO 81
<211> LENGTH: 10
<212> TYPE: PRT
<213> ORGANISM: HIV-1

<400> SEQUENCE: 81

Lys Val Ile Val Gly Ile Gly Gly Phe Ile
1               5                   10

<210> SEQ ID NO 82
<211> LENGTH: 10
<212> TYPE: PRT
<213> ORGANISM: HIV-1

<400> SEQUENCE: 82

Val Leu Val Gly Pro Thr Pro Val Asn Ile
1               5                   10

<210> SEQ ID NO 83
<211> LENGTH: 10
<212> TYPE: PRT
<213> ORGANISM: HIV-1

<400> SEQUENCE: 83

Val Leu Val Gly Pro Thr Pro Thr Asn Val
1               5                   10

<210> SEQ ID NO 84
<211> LENGTH: 9
<212> TYPE: PRT
<213> ORGANISM: HIV-1

<400> SEQUENCE: 84

Val Leu Ala Glu Ala Met Ser Gln Val
1               5
```

```
<210> SEQ ID NO 85
<211> LENGTH: 9
<212> TYPE: PRT
<213> ORGANISM: HIV-1

<400> SEQUENCE: 85

Val Leu Ala Glu Ala Met Ser Gln Ala
1               5

<210> SEQ ID NO 86
<211> LENGTH: 9
<212> TYPE: PRT
<213> ORGANISM: HIV-1

<400> SEQUENCE: 86

Val Leu Ala Glu Ala Met Ser Gln Ile
1               5

<210> SEQ ID NO 87
<211> LENGTH: 9
<212> TYPE: PRT
<213> ORGANISM: HIV-1

<400> SEQUENCE: 87

Lys Leu Thr Pro Leu Cys Val Thr Leu
1               5

<210> SEQ ID NO 88
<211> LENGTH: 9
<212> TYPE: PRT
<213> ORGANISM: HIV-1

<400> SEQUENCE: 88

Lys Leu Thr Pro Leu Cys Val Pro Leu
1               5

<210> SEQ ID NO 89
<211> LENGTH: 9
<212> TYPE: PRT
<213> ORGANISM: Influenza

<400> SEQUENCE: 89

Ala Ser Asn Glu Asn Met Glu Thr Met
1               5

<210> SEQ ID NO 90
<211> LENGTH: 10
<212> TYPE: PRT
<213> ORGANISM: Influenza

<400> SEQUENCE: 90

Ser Ser Leu Glu Asn Phe Arg Ala Tyr Val
1               5                   10

<210> SEQ ID NO 91
<211> LENGTH: 9
<212> TYPE: PRT
<213> ORGANISM: Influenza

<400> SEQUENCE: 91

Ala Ser Asn Glu Asn Met Glu Thr Met
1               5

<210> SEQ ID NO 92
<211> LENGTH: 9
<212> TYPE: PRT
```

<213> ORGANISM: Influenza

<400> SEQUENCE: 92

Ala Ser Asn Glu Asn Met Asp Ala Met
1               5

<210> SEQ ID NO 93
<211> LENGTH: 12
<212> TYPE: PRT
<213> ORGANISM: Influenza

<400> SEQUENCE: 93

Ser Phe Tyr Arg Asn Val Val Trp Leu Ile Lys Lys
1 5 10

<210> SEQ ID NO 94
<211> LENGTH: 12
<212> TYPE: PRT
<213> ORGANISM: Influenza

<400> SEQUENCE: 94

Ser Phe Phe Arg Asn Val Val Trp Leu Ile Lys Lys
1 5 10

<210> SEQ ID NO 95
<211> LENGTH: 12
<212> TYPE: PRT
<213> ORGANISM: Influenza

<400> SEQUENCE: 95

Ser Phe Leu Arg Asn Val Val Trp Leu Ile Lys Lys
1 5 10

<210> SEQ ID NO 96
<211> LENGTH: 9
<212> TYPE: PRT
<213> ORGANISM: Influenza

<400> SEQUENCE: 96

Ala Ser Asn Glu Asn Met Glu Thr Met
1 5

<210> SEQ ID NO 97
<211> LENGTH: 10
<212> TYPE: PRT
<213> ORGANISM: Influenza

<400> SEQUENCE: 97

Ser Ser Leu Glu Asn Phe Arg Ala Tyr Val
1 5 10

<210> SEQ ID NO 98
<211> LENGTH: 10
<212> TYPE: PRT
<213> ORGANISM: Influenza

<400> SEQUENCE: 98

Ser Ser Ala Glu Asn Phe Arg Ala Tyr Val
1 5 10

<210> SEQ ID NO 99
<211> LENGTH: 10
<212> TYPE: PRT
<213> ORGANISM: Influenza

<400> SEQUENCE: 99

```
Ser Ser Leu Glu Asn Phe Ala Ala Tyr Val
1               5                   10

<210> SEQ ID NO 100
<211> LENGTH: 9
<212> TYPE: PRT
<213> ORGANISM: Epstein-Barr Virus

<400> SEQUENCE: 100

Tyr Leu Ala Gly Leu Leu Thr Met Val
1               5

<210> SEQ ID NO 101
<211> LENGTH: 9
<212> TYPE: PRT
<213> ORGANISM: EBV

<400> SEQUENCE: 101

Cys Leu Ala Gly Leu Leu Thr Met Val
1               5

<210> SEQ ID NO 102
<211> LENGTH: 9
<212> TYPE: PRT
<213> ORGANISM: EBV

<400> SEQUENCE: 102

Cys Leu Gly Gly Leu Leu Thr Met Val
1               5

<210> SEQ ID NO 103
<211> LENGTH: 9
<212> TYPE: PRT
<213> ORGANISM: EBV

<400> SEQUENCE: 103

Gly Leu Cys Thr Leu Val Ala Met Leu
1               5

<210> SEQ ID NO 104
<211> LENGTH: 8
<212> TYPE: PRT
<213> ORGANISM: EBV

<400> SEQUENCE: 104

Leu Leu Trp Thr Leu Val Val Leu
1               5

<210> SEQ ID NO 105
<211> LENGTH: 10
<212> TYPE: PRT
<213> ORGANISM: Heptatitis B Virus

<400> SEQUENCE: 105

Phe Leu Pro Ser Asp Phe Phe Pro Ser Val
1               5                   10

<210> SEQ ID NO 106
<211> LENGTH: 10
<212> TYPE: PRT
<213> ORGANISM: HBV

<400> SEQUENCE: 106

Phe Leu Pro Asn Asp Phe Phe Pro Ser Val
1               5                   10
```

```
<210> SEQ ID NO 107
<211> LENGTH: 10
<212> TYPE: PRT
<213> ORGANISM: HBV

<400> SEQUENCE: 107

Phe Leu Pro Asn Asp Phe Phe Pro Ser Ala
1               5                   10

<210> SEQ ID NO 108
<211> LENGTH: 10
<212> TYPE: PRT
<213> ORGANISM: HBV

<400> SEQUENCE: 108

Phe Leu Pro Val Asp Phe Phe Pro Ser Val
1               5                   10

<210> SEQ ID NO 109
<211> LENGTH: 10
<212> TYPE: PRT
<213> ORGANISM: HBV

<400> SEQUENCE: 109

Phe Leu Pro Ala Asp Phe Phe Pro Ser Val
1               5                   10

<210> SEQ ID NO 110
<211> LENGTH: 10
<212> TYPE: PRT
<213> ORGANISM: HBV

<400> SEQUENCE: 110

Phe Leu Pro Ala Asp Phe Phe Pro Ser Ile
1               5                   10
```

METHODS AND COMPOSITIONS FOR POLYTOPIC VACCINATION

The invention described herein was made with government support under grant number CTS-0243520 from the National Science Foundation. Accordingly, the United States government has certain rights in this invention.

1. FIELD OF THE INVENTION

The present invention relates to methods and compositions for therapeutic and prophylactic vaccination. The methods of the invention overcome the deleterious effects of immunodominance and provide more effective immunity against infectious agents, particularly multi-strain infectious agents.

2. BACKGROUND OF THE INVENTION

A significant problem in vaccine development is overcoming the effects of the poorly understood phenomenon of immunodominance. Although a particular infectious agent comprises hundreds or thousands of potentially antigenic molecules, each comprising multiple protein or peptide epitopes capable of binding to antibodies or to MHC molecules, the immune response elicited against a particular infectious agent, is often directed against only a limited number of epitopes, or even to a single epitope (see van der Most et al., J. Immunol. 1996 157:5543-54 and references infra). These epitopes are referred to as "immunodominant" epitopes. Such a narrow immune response to a few immunodominant epitopes offers poor protection against subsequent infection by a mutated form or by different strains of the original infectious agent. The problem of immunodominance is especially acute for infectious agents having a high mutation rate and for those comprising multiple strains.

For reasons that are not well understood, the immune response elicited by some immunodominant epitopes actually impairs the ability to develop an effective response against a subsequent infection. This has been observed, for example, with infectious diseases caused by multi-strain pathogens. This phenomenon, also referred to as "original antigenic sin," was first characterized with respect to the influenza virus (Fazekas de St. Groth and Webster, 1966 J. Exp. Med. 124:331-45), and has since been observed in hepatitis B and C (Harcourt et al., 2003 Clin. Exp. Immunol. 131:122-29), malaria (Good et al., 1993 Parasite Immunol. 15:187-93), dengue fever (Rothman et al., 2001 Vaccine 19, 4694-4699), *Chlamydia* (Berry et al., 1999 J. Infec. Dis. 179:180-86), and HIV (Anderson et al., 2001 Clin. Immunol. 101:152-57). For example, immunity after infection by a particular strain of dengue virus protects only modestly or even negatively against reinfection by one of the other three strains (Mongkolsapaya et al. 2003 Nature Medicine 9:921-27). This effect has also been observed for subsequent infections by a different pathogen. For example, exposure to influenza appears to increase susceptibility to hepatitis C through immunodominance (Brehm et al. 2002 NI 3:627-34). The existence of this phenomenon means that for some infectious diseases, vaccinated individuals may paradoxically be more susceptible to infection by another strain of the same pathogen, or even to another pathogen, than individuals who were not vaccinated. An effect similar to original antigenic sin has also been observed in the context of tumor immunity (Makki et al. 2002 Cancer Immunity 2:4-17, and references infra; see also Cole et al. 1997 J. Immunol. 158: 4301-09 and van der Most et al. 1996 J. Immunol. 157:554354). Makki et al. suggest that vaccination with certain dominant tumor antigens not only fails to elicit an immune response against the tumor, but also hinders the development of an effective response against other, presumably subdominant tumor antigens.

Immunodominance has also been observed in the context of tumor immunity. For example, an existent response to a tumor antigen may prevent a response to new tumor antigens arising through mutation. Schreiber et al. refers to this phenomenon as the "priority of the first response" which was suggested by experiments in mice showing that repeated immunization with an antigen A, followed by later immunization with an antigen B, fails to elicit an anti-B response (Schreiber et al. 2002 Cancer Biol. 12:25-31, and references infra). This immunodominance could be broken experimentally by vaccination with individual tumor antigens at separate sites, rather than with multiple antigens at one site.

One factor in determining whether an epitope becomes dominant appears to be its effectiveness in generating an immune response (Schreiber et al., Cancer Biol. 2002 12:25-31). This is a function of a number of factors, including the binding affinity of the epitope for T cell receptors or for antibodies expressed by B cells. Intracellular processing of peptide antigens is also a factor because epitopes which are presented at high levels on the surface of antigen presenting cells tend to elicit a stronger response. However, it is not simply the case that the dominant epitopes are able to elicit an immune response, and subdominant epitopes are not. The ability of subdominant epitopes to elicit an immune response has been demonstrated, for example, in the context of viral infections and tumor immunity (see Cole et al, J. Immunol. 1997 158:4301-09; van der Most et al., J. Immunol. 1996 157:5543-54; Makki et al., Cancer Immunity 2002 2:4-17 and references infra). Makki et al. suggests that, in the context of tumor immunity, vaccination with a subdominant epitope may even be superior to vaccination with a dominant epitope.

It is not known why subdominant epitopes which are capable of eliciting an immune response nevertheless often fail to do so. However, there is evidence that dominant epitopes can suppresses immunity to the other, subdominant epitopes. This phenomenon may be a result of the manner in which antigen-specific effector cells are selected. For example, cytotoxic T cells ("CTLs" or "CD8+ T cells") binding to MHC-peptide complexes on an antigen presenting cell can inhibit the proliferation of other CTLs binding to other complexes on the same cell. Since such binding is required to stimulate T cell proliferation, and only proliferating T cells mature into memory T cells, the effect is presumably to produce narrowing of the repertoire of memory T cells. Thus, the ability to protect against a secondary infection by a similar but not identical infectious agent is reduced. This and other aspects of the cellular biology and immunology of immuodominance in the cytotoxic T cell response against viral infections are reviewed by Yewdell and Del Val, Immunity 2004 2:149-53.

There remain fundamental unanswered questions that have hindered the design of effective vaccines or vaccination strategies that will effectively avoid the adverse effects of immunodominance. For example, the relationship between antibody or T cell receptor binding, the sequence of the antigen, and the emergence of immunodominance is not known. Understanding these relationships is important to vaccine design generally and is of particular importance to the development of safe, effective peptide-based vaccines. For a review of epitope identification, vaccine design and delivery, see Sette and Fikes, 2003 Cur. Opinion Immunol. 15:461-70.

One approach to answering these questions is to utilize mathematical models that capture the sequence-level dynamics of the effector cell and epitope binding interactions. A random energy model is one such mathematical model which has successfully reproduced complex immune phenomena such as immunodominance and original antigenic sin. This model captures much of the thermodynamics of protein folding and ligand binding, and consequently also captures the correlations between the three dimensional amino acid structure of antibodies or T cell receptors and the amino acid sequences of antigenic molecules. The specific antibody or T cell repertoire of an individual is represented in the model by a specific set of amino acid sequences. An epitope of a specific antigen or viral strain is represented by a specific instance of the random parameters. An immune response that finds a T cell receptor or antibody with a high binding affinity to a specific epitope corresponds in the model to finding an amino acid sequence having a low energy for a specific parameter set.

The robustness of the model as a tool for accurately simulating the interactions between effector cells and antigens has been demonstrated by a number of experiments. For example, Deem and Lee demonstrated that original antigenic sin in the context of influenza stems from the localization of the immune system response in antibody sequence space (Phys. Rev. Lett. 2003 91:68101-104). This localization stems from memory sequences being less able to evolve than naïve sequences, and is observed in general for diseases with high year-to-year mutation rates, such as influenza. Building on these results, Deem and Munoz demonstrated that this localization played a role in the ineffectiveness of the 2003-2004 influenza vaccine in the United States (Vaccine 2005 23:1144-48). Predictions from the model also correlated well with the efficacies of the H3N2 influenza A component of the annual vaccine between 1971 and 2004 (Gupta and Deem 2005 Quant. Biol., document no. 0503030). In fact, the predictive value of the model was superior to that of the standard ferret animal model.

In another example, the model was used to examine cross-reactivity in the T cell response to mutated viral antigens (Park and Deem 2004 Physica A. 341:455-70). Here again, the predicted specific lysis curves were in excellent agreement with ex vivo and in vitro altered peptide ligand experiments. Predictions from the model of immunodominance in the human immune response to the four-component dengue vaccine also accurately predicted experimental results (Deem 2004 AIChE J. 50:734-38).

It is clear from these results that the model is able to accurately simulate important aspects of the immune response to an antigen and thereby provide insights for vaccine design and development. The present invention is based in part on such an insight from the model, namely that multi-site vaccination against an infectious agent increases immunity against subdominant epitopes, thereby mitigating the effects of immunodominance.

3. SUMMARY OF THE INVENTION

The invention provides a method of treating or preventing an infectious disease in a subject comprising administering to the subject a plurality of compositions, each composition being administered to a different site of the subject, wherein each composition comprises at least one antigenic molecule, wherein at least one antigenic molecule in each composition comprises one or more epitopes of the same infectious agent or a strain thereof, and wherein the one or more molecules of each composition comprise in aggregate a set of epitopes distinct from that of any other composition so administered, wherein each site is, or substantially drains to, an anatomically distinct bodily part selected from the group consisting of a lymph node, a group of lymph nodes, a nonencapsulated cluster of lymphoid tissue, and the spleen, and wherein the infectious agent causes the infectious disease.

The invention also provides a method of treating or preventing an infectious disease in a subject comprising administering to the subject a plurality of compositions, each composition being administered to a different site of the subject wherein each composition comprises at least one antigenic molecule, wherein at least one antigenic molecule in each composition comprises one or more epitopes of the same infectious agent or a strain thereof, and wherein the one or more molecules of each composition comprise in aggregate a set of epitopes distinct from that of any other composition so administered, wherein the distance between each pair of sites is greater than the distance between any two anatomically distinct lymph nodes or groups of lymph nodes nearest each site, and wherein the infectious agent causes the infectious disease.

The invention also provides a method of treating or preventing one or more infectious diseases in a subject comprising administering to the subject a plurality of compositions, each composition being administered to a different site of the subject wherein each composition comprises at least one purified antigenic molecule, wherein at least one purified antigenic molecule in each composition comprises one or more epitopes of one or more infectious agents or strains thereof, the epitopes having an epitopic variance of between 0.05 and 0.50, and wherein the one or more purified antigenic molecules of each composition comprise in aggregate a set of epitopes distinct from that of any other composition so administered, wherein the distance between each pair of sites is greater than the distance between any two anatomically distinct lymph nodes or groups of lymph nodes nearest each site, wherein said one or more infectious agents cause the one or more infectious diseases.

The invention further provides a method for determining whether a vaccine composition suppresses immunodominance in a subject comprising (a) administering to the subject a plurality of compositions, each composition being administered to a different site of the subject wherein each composition comprises at least one antigenic molecule, wherein at least one antigenic molecule in each composition comprises one or more epitopes of the same infectious agent or a strain thereof, and wherein the one or more molecules of each composition comprise in aggregate a set of epitopes distinct from that of any other composition so administered, wherein the distance between each site is greater than the distance between any two anatomically distinct lymph nodes or groups of lymph nodes nearest each site; and (b) measuring an immune response to the at least one antigenic molecule of each composition so administered, wherein immunodominance has been suppressed in the subject if the ratio between the immune response of the most immunogenic composition and the least immunogenic composition is reduced compared to the ratio obtained with administration of all of the compositions at a single site.

The invention also provides a kit comprising in separate containers at least two compositions, each composition comprising at least one antigenic molecule and each antigenic molecule comprising one or more epitopes of the same infectious agent or a strain thereof, wherein the one or more molecules of each composition comprise in aggregate a set of epitopes distinct from that of said other composition or compositions, and instructions for administering each composition to a separate site of a subject.

The invention also provides a kit comprising in separate containers at least two compositions, each composition comprising at least one purified antigenic molecule, and each purified antigenic molecule comprising one or more epitopes of one or more infectious agents or strains thereof, the epitopes having an epitopic variance of between 0.05 and 0.50, wherein the one or more purified antigenic molecules of each composition comprise in aggregate a set of epitopes distinct from that of said other composition or compositions, and instructions for administering each composition to a separate site of a subject.

4. BRIEF DESCRIPTION OF THE FIGURES

FIG. 1: Specific lysis ratios for the least to the most dominant epitope of the four strains of dengue fever. The error bars are given by standard error analysis of the experimental error bars.

FIG. 2(*a*)-(*c*): (a) Evolved clearance probability to a second strain after exposure to an original strain that differs in the epitope amino acid sequence by fraction $p_{epitope}$ (solid line). The primary response in the absence of a vaccine is shown (dashed line, independent of $p_{epitope}$). For dengue, $p_{epitope}$=0.5/9 (circle). (b) During a secondary response for dengue, memory T cell receptors are initially better but eventually worse after selection than are naïve T cell receptors ($p_{epitope}$=0.5/9). This result explains the cause of original antigenic sin. (c) The immunodominance among the four strains under different conditions. Left column: four strains independently evolve during a primary response, and the immunodominance due to the heterologous nature of immunity is measured. That is, the response to strain i is measured after a primary vaccination against strain i. Middle columns: the $i^{th}$ column shows the response to the four strains after a primary vaccination against strain i. Note the immunodominance. That is, the response to strain j is measured after a primary vaccination against strain i. Right columns: initial primary response to strain i for the $i^{th}$ column, followed by a secondary response as in the left column. That is, the response to strain j is measured after a primary vaccination against strain i and a secondary vaccination against strain j. For each column, the strains are ranked in order of immunodominance.

FIG. 3: Predictions of the theory for a polytopic four-component dengue vaccine, $p_{epitope}$=0.5/9, when the different strains are injected in different physical locations and evoke an immune response that evolves independently in different lymph nodes until mixing round after which the lymph system is well-mixed.

FIG. 4(*a*)-(*d*): $p_{epitope}$=0.5/9. (a) Immunodominance for a four-component dengue vaccine. (b) Reduced immunodominance for a primary single-component dengue vaccine (strain i in the $i^{th}$ column), followed by a secondary four-component dengue vaccine. (c) Reduced immunodominance for a polytopic four-component dengue vaccine, with each component administered to a distinct lymph node (mixing round=9). (d) Reduced immunodominance for a primary single-component dengue vaccine (strain i in the $i^{th}$ column), followed by a secondary polytopic four-component dengue vaccine (mixing round=9). An improved response to the subdominant strain provides the most immunological benefit in the case of dengue; this response is improved 101% in d) versus a).

FIG. 5(*a*)-(*d*): $p_{epitope}$=1.0/9. (a) Immunodominance for a four-component dengue vaccine. (b) Reduced immunodominance for a primary single-component dengue vaccine (strain i in the $i^{th}$ column), followed by a secondary four-component dengue vaccine. (c) Reduced immunodominance for a polytopic four-component dengue vaccine, with each component administered to a distinct lymph node (mixing round=9). (d) Reduced immunodominance for a primary single-component dengue vaccine (strain i in the $i^{th}$ column), followed by a secondary polytopic four-component dengue vaccine (mixing round=9). An improved response to the subdominant strain provides the most immunological benefit in the case of dengue; this response is improved 290% in d) versus a).

FIG. 6(*a*)-(*b*): (a) For the highest affinity T cell receptor, the binding constant fluctuates between $10^5$ l/mol and $10^7$ l/mol. (b) Most binding constants differ within a factor of 10 for the 0.5% of the antigen specific T cells selected to be memory T cells.

FIG. 7: Flow diagram of the T cell receptor selection dynamics in the Generalized NK model.

5. DETAILED DESCRIPTION OF THE INVENTION

This invention provides methods for treating or preventing an infectious disease in a subject by eliciting an immune response against an infectious agent which causes the disease. The terms "elicit," "stimulate," and "induce" are used interchangeably to denote the generation of a de novo immune response in a subject or to denote the enhancement of the strength or persistence of an existing immune response. An infectious agent may be, for example, a pathogen, such as a bacterium, a virus, or a parasite. An infectious agent may be a strain of a pathogen, particularly a strain of a virus. Infectious agents and strains are described in more detail in Section 5.3.

The methods comprise administering to the subject a plurality of compositions, each composition being administered to a different site of the subject, preferably a human subject, wherein each composition comprises at least one antigenic molecule. In one embodiment, at least one antigenic molecule in each composition comprises one or more epitopes of the same infectious agent or a strain thereof and the one or more molecules of each composition comprise in aggregate a set of epitopes distinct from that of any other composition administered to the subject. In another embodiment, at least one antigenic molecule in each composition comprises one or more epitopes of one or more infectious agents, which can be the same or different infectious agents, or strains thereof, the epitopes having an epitopic variance of between 0.05 and 0.50, and wherein the one or more molecules of each composition comprise in aggregate a set of epitopes distinct from that of any other composition so administered. In a specific embodiment, the one or more antigenic molecules are purified; thus, in such an embodiment, for example, the antigenic molecules are not contained in whole viral particles. In one embodiment, the epitopes have an epitopic variance of between 0.05 and 0.25. In one embodiment, each site is, or substantially drains to, an anatomically distinct bodily part selected from the group consisting of a lymph node, a group of lymph nodes, a nonencapsulated cluster of lymphoid tissue, and the spleen. In another embodiment, the distance between each pair of sites is greater than the distance between any two anatomically distinct lymph nodes or groups of lymph nodes nearest each site. A more detailed description of the sites and methods of administration, epitopes and antigenic molecules, infectious agents, and pharmaceutical compositions provided by the invention is set forth in the sections that follow.

In one embodiment, the plurality of compositions comprises 2-10 compositions. In a preferred embodiment, the plurality of compositions comprises three or four compositions. In a preferred embodiment, the compositions are administered to the subject at substantially the same time. In one embodiment, the total time between the first administration and the last administration is 5 or fewer days. The compositions may comprise dominant or subdominant epitopes. In certain embodiments, at least one composition is administered prior to the other compositions, for example more than 6 days, more than 14 days, or within 6 months before the other compositions. In a preferred embodiment, at least one composition is administered 6-14 days, 1-3 months, 3-6 months, 6-9 months, or 9-12 months prior to the other compositions. Preferably, the composition administered early comprises one or more subdominant epitopes.

In one embodiment, each composition comprises at least one antigenic molecule comprising one or more epitopes of a strain of a virus causing the infectious disease, and no two compositions comprise epitopes of the same strain. In one embodiment, each composition comprises at least one purified antigenic molecule comprising one or more epitopes of one or more viral strains causing the one or more infectious diseases, and no two compositions comprise epitopes of the same strains. In one embodiment, each composition comprises at least one antigenic molecule comprising one or more epitopes of a strain of a virus causing the infectious disease, and at least two compositions do not comprise epitopes of the same strain. In one embodiment, each composition comprises at least one purified antigenic molecule comprising one or more epitopes of one or more viral strains causing the one or more infectious diseases, and at least two compositions do not comprise epitopes of the same strain. In one embodiment, each composition comprises at least one antigenic molecule comprising one or more epitopes of a strain of a virus causing the infectious disease, and no two compositions comprise the same epitopes. In one embodiment, each composition comprises at least one purified antigenic molecule comprising one or more epitopes of one or more viral strains causing the one or more infectious diseases, and no two compositions comprise the same epitopes. In another embodiment, each composition comprises at least one antigenic molecule comprising one or more subdominant epitopes of an infectious agent causing the infectious disease. In one embodiment, each composition comprises at least one purified antigenic molecule comprising one or more subdominant epitopes of one or more infectious agents causing the one or more infectious diseases. In one embodiment, at least one antigenic molecule comprises one or more dominant epitopes of an infectious agent causing the infectious disease. In one embodiment, each composition comprises at least one purified antigenic molecule comprising one or more dominant epitopes of one or more infectious agents causing the one or more infectious diseases.

In one embodiment, the set of epitopes of each composition differs from every other set by an epitopic variance defined as the sum of the number of non-conservative amino acid changes and one half of the number of conservative amino acid changes divided by the total number of amino acids in the epitope, and wherein the epitopic variance between the epitopes of each composition is between 0.02 and 1. In another embodiment, the epitopic variance between the set of epitopes of each composition is between 0.05-0.95, between 0.05-0.75, between 0.05-0.50, or between 0.02-0.40. Preferably, the epitopic variance among the epitopes within the same composition is less than 0.10.

In one embodiment, each antigenic molecule is a peptide, the amino acid sequence of which consists of 25 amino acids or less. In one embodiment, each antigenic molecule is a peptide, the amino acid sequence of which consists of 12 amino acids or less. In specific embodiments, the peptide consists of 8-11 amino acids, 10-18 amino acids, or 8-18 amino acids. Preferably, the peptide is a T cell epitope or a B cell epitope, and most preferably a cytotoxic T cell epitope. In one embodiment, the epitopes are overlapping epitopes for different MHC alleles. In another embodiment, the epitopes are epitopes of different MHC alleles.

In one embodiment, each site to which a composition is administered is or drains to a lymph node or group of lymph nodes selected from the group consisting of the lymph nodes of the head and neck, the axillary lymph nodes, the tracheobronchial lymph nodes, the parietal lymph nodes, the gastric lymph nodes, the ileocolic lymph nodes, and the inguinal and subinguinal lymph nodes. In another embodiment, the sites are selected from the group consisting of the right arm, the left arm, the right thigh, the left thigh, the right shoulder, the left shoulder, the right breast, the left breast, the abdomen, the right buttock, and the left buttock. In one embodiment, the site is or drains to a nonencapsulated cluster of lymphoid tissue selected from the group consisting of the tonsils, the adenoids, the appendix, and Peyer's patches. In a specific embodiment, at least one composition is administered to a site that drains to the spleen.

In one embodiment, each composition is administered by a route independently selected from the group consisting of intradermally, subcutaneously, transdermally, intramuscularly, orally, rectally, vaginally, by inhalation, and a combination thereof. In another embodiment, each composition is administered by a route independently selected from the group consisting of intradermally, subcutaneously, transdermally, intramuscularly, and a combination thereof. In one embodiment, at least one composition is injected directly into an anatomically distinct lymph node, lymph node cluster, or nonencapsulated cluster of lymphoid tissue.

In one embodiment, the methods of the invention further comprise administering to the subject antigen presenting cells which have been sensitized with at least one antigenic molecule of a composition. In a preferred embodiment, the antigen presenting cells are dendritic cells. In one embodiment, the method further comprises administering to the subject one or more adjuvants. In one embodiment, at least one composition further comprises one or more adjuvants. In one embodiment, the one or more adjuvants is selected from the group consisting of an oil-based adjuvant, a CpG DNA adjuvant, a mineral salt adjuvant, a mineral salt gel adjuvant, a particulate adjuvant, a microparticulate adjuvant, a mucosal adjuvant, and a cytokine. Further examples of adjuvants encompassed by the invention are provided by Section 5.4. Such adjuvants may either be formulated with the compositions of the invention or administered separately from the compositions, e.g., prior to, concurrently with, or after the compositions are administered to the subject.

In one embodiment, the prophylactic or therapeutic methods of the invention are administered to prevent or treat an infectious disease caused by an infectious agent which is a virus, a bacterium, a protozoan, or a parasite. In one embodiment, the virus is selected from the group consisting of a lymphocytic choriomeningitis virus, a hepatitis B virus, an Epstein Barr virus, an influenza virus, and a human immunodeficiency virus. In one embodiment, the virus is selected from the group consisting of the Flaviviridae family of viruses. In a specific embodiment, the flavivirus is selected from the group consisting of dengue, Kunjin, Japanese encephalitis, West Nile, and yellow fever virus. In a preferred embodiment, the virus is a dengue virus. Additional non-limiting examples of infectious agents encompassed by the methods of this invention are provided in Section 5.3.

The invention also provides a method for determining whether a vaccine composition suppresses immunodominance in a subject comprising administering to the subject a plurality of compositions, each composition being administered to a different site of the subject and each composition comprising at least one antigenic molecule as described herein, and measuring any immune response to the antigenic molecule or molecules of each composition so administered. The subject may be a human subject or a non-human jawed vertebrate. Immunodominance has been suppressed in the subject if the ratio between the immune response to the most immunogenic composition and the least immunogenic composition is reduced compared to the ratio obtained with administration of all of the compositions at a single site. In a preferred embodiment, the ratio is reduced by about 20%, about 50%, about 75%, or about 95%. Any routine assay for measuring an immune response to an antigenic molecule may be used in accordance with this embodiment. Preferably, the assay measures a cytotoxic T cell response to the antigenic molecules of each composition, for example using a tetramer assay or a chromium release assay. Further examples of methods for measuring immunodominance by measuring an immune response are provided in Section 5.6.

The invention also provides a kit comprising in separate containers at least two compositions, each composition comprising at least one antigenic molecule and each antigenic molecule comprising one or more epitopes of the same infectious agent or a strain thereof, wherein the one or more molecules of each composition comprise in aggregate a set of epitopes distinct from that of said other composition or compositions, and instructions for administering each composition to a separate site of a subject. In one embodiment, each composition comprises at least one purified antigenic molecule, and each purified antigenic molecule comprises one or more epitopes of one or more infectious agents or strains thereof, the epitopes having an epitopic variance of between 0.05 and 0.50. In a preferred embodiment, the kit comprises three or four compositions. In another preferred embodiment, the kit further comprises in one or more additional containers an anti-viral agent, an anti-bacterial agent, a cytokine, or an adjuvant. The kits provided by the invention are described more fully in section 5.4.4.

The following sections provide a further description of various aspects of the invention including sites of administration, epitopes of antigenic molecules, infectious agents, pharmaceutical compositions, combination therapy, and methods of measuring and monitoring immunodominance.

5.1 Sites of Administration

The methods of the present invention encompass administering a plurality of compositions to separate sites of a subject. In a preferred embodiment, each site is, or substantially drains to, an anatomically distinct bodily part selected from a lymph node, a group of lymph nodes, a nonencapsulated cluster of lymphoid tissue, or the spleen. In another preferred embodiment, the distance between each site is greater than the distance between any two anatomically distinct lymph nodes or groups of lymph nodes nearest each site.

In one embodiment, the sites of administering are selected from the group consisting of the head, the neck, the right arm, the left arm, the right thigh, the left thigh, the right buttock, the left buttock, and the abdomen, and combinations thereof. The sites may also be chosen to administer one or more compositions to an internal organ which substantially drains to a particular group of lymph nodes, for example, the lungs, the stomach, the intestines, or the rectum.

In one embodiment, one or more sites of administering are selected to drain to one or more of the superficial lymph nodes of the head and neck. The superficial lymph nodes of the head and neck include, for example, the inferior deep cervical glands, the superior deep cervical glands, the superficial cervical glands, the submental glands, the submaxillary glands, the supramandibular glands, the buccinator glands, the parotid glands, the maxillary glands, the posterior auricular glands, and the occipital glands.

In one embodiment, one or more sites of administering are selected to drain to one or more of the axillary lymph nodes (lymphoglandulae axillares). The axillary lymph nodes include, for example, the lateral group which drains most of the arm; the anterior or pectoral group which drains the skin and muscles of the anterior and lateral thoracic walls as well as the central and lateral parts of the mamma; the posterior or subscapular group which drains the skin and muscles of the lower part of the back of the neck and of the posterior thoracic wall; the central or intermediate group of three or four large glands which drains to the subclavicular group; and the medial or subclavicular group which drains to the upper peripheral part of the mamma, but which receives the efferents of all the other axillary glands. Preferably, if one site of administering drains to the medial or subclavicular group, the other sites do not drain to the axillary lymph nodes.

In one embodiment, one or more sites of administering are selected to drain to one or more of the tracheobronchial lymph nodes. These glands drain the lungs and bronchi, the thoracic part of the trachea, and the heart.

In one embodiment, one or more sites of administering are selected to drain to one or more of the lymph nodes of the stomach or colon, including for example the gastric glands, the subpyloric glands, the pancreatic glands, and the ileocolic glands.

In one embodiment, one or more sites of administering are selected to drain to one or more of the superficial glands of the lower extremity, for example, the inguinal and the subinguinal glands.

In one embodiment, one or more sites of administering are selected to drain to a nonencapsulated cluster of lymphoid tissue, for example, the tonsils and adenoids, the appendix, or Peyer's patches.

The methods of the invention provide for the administration of a plurality of compositions, each to a different site. In a preferred embodiment, the number of compositions administered is 2, 3, 4, or 5. Further examples are provided in Section 5.4.1., Methods of Administration.

In a specific example, the method comprises administering two compositions, each composition being administered to a different site, wherein the first site is selected to drain to one or more of the axillary lymph nodes and the second site is selected to drain to one or more of the inguinal lymph nodes (inguinal or subinguinal).

In another specific example, the method comprises administering three compositions, each composition being administered to a different site, wherein the first site is selected to drain to one or more of the axillary lymph nodes, the second site is selected to drain to one or more of the inguinal lymph nodes (inguinal or subinguinal), and the third site is selected to drain to one or more of the superficial lymph nodes of the head and neck. In another embodiment, the three sites of administering are selected to drain to one or more lymph nodes selected from the group consisting of the axillary lymph nodes of the left arm, the axillary lymph nodes of the right arm, the inguinal lymph nodes of the left leg, the inguinal lymph nodes of the right leg, the tracheobronchial lymph nodes, and the superficial lymph nodes of the head and neck.

In another specific example, the method comprises administering four compositions, each composition being administered to a different site, wherein the first site is selected to drain to one or more of the axillary lymph nodes, the second site is selected to drain to one or more of the superficial lymph nodes of the head and neck, the third site is selected to drain to one or more of the tracheobronchial lymph nodes, and the fourth site is selected to drain to one or more of the superficial glands of the lower extremity, for example, the inguinal and the subinguinal glands. In another embodiment, the four sites of administering are selected to drain to one or more lymph nodes selected from the group consisting of the axillary lymph nodes of the left arm, the axillary lymph nodes of the right arm, the inguinal lymph nodes of the left leg, the inguinal lymph nodes of the right leg, the tracheobronchial lymph nodes, and the superficial lymph nodes of the head and neck.

In a further specific example the method comprises administering five compositions, each composition being administered to a different site, wherein the first site is selected to drain to one or more of the axillary lymph nodes, the second site is selected to drain to one or more of the superficial lymph nodes of the head and neck, the third site is selected to drain to one or more of the tracheobronchial lymph nodes, the fourth site is selected to drain to one or more of the superficial glands of the lower extremity, for example, the inguinal and the subinguinal glands, and the fifth site is selected to drain to one or more gastric glands. In another embodiment, the five sites of administering are selected to drain to one or more lymph nodes selected from the group consisting of the axillary lymph nodes of the left arm, the axillary lymph nodes of the right arm, the inguinal lymph nodes of the left leg, the inguinal lymph nodes of the right leg, the tracheobronchial lymph nodes, the superficial lymph nodes of the head and neck, the gastric glands, the subpyloric glands, and the pancreatic glands.

5.2 Antigenic Molecules and Epitopes

The methods of the invention are useful for treating or preventing an infectious disease in a subject by eliciting an immune response against an infectious agent which causes the disease. The methods comprise administering to the subject a plurality of compositions, each composition comprising at least one antigenic molecule. In one embodiment, each antigenic molecule of a composition comprises one or more epitopes of the same infectious agent or a strain thereof. In another embodiment, each antigenic molecule of a composition comprises one or more epitopes of one or more infectious agents, which can be the same or a different infectious agent, or strains thereof, the epitopes having an epitopic variance of between 0.05 and 0.50. In a specific embodiment, the one or more antigenic molecules of the composition are purified; thus, in such an embodiment, for example, the antigenic molecules are not contained in whole viral particles. The plurality of compositions to be administered is selected so that the one or more antigenic molecules of each composition comprise in aggregate a distinct set of epitopes. Thus, according to the methods of the invention, no two compositions comprise the same set of epitopes.

As used herein, an epitope is a portion of an antigenic molecule capable of eliciting an immune response to the molecule, preferably a cytotoxic T cell response or an antibody-secreting B cell mediated response, or which can be bound by an antibody. The terms "epitope" and "antigenic determinant" are used interchangeably herein. The term "antigenic" in the context of a molecule refers to the ability of the molecule to elicit, stimulate, or induce an immune response to itself, or to be bound by an antibody. Antigenic molecules are usually proteinaceous molecules such as proteins or polypeptides. The terms "peptide," "polypeptide," and "protein" are used interchangeably herein. However, antigenic molecules may also comprise or consist of other molecules such as carbohydrates, lipids, nucleic acids, or small organic molecules. Small organic molecules preferably comprise one or more cyclic ring structures. Antigenic molecules may also comprise one or more of the foregoing kinds of molecules, for example, an antigenic molecule can be a glycoprotein, a lipoprotein, a lipopolysaccharide, or a ribonucleic acid.

Preferably, the one or more antigenic molecules of the compositions administered according to the methods of the invention are purified from contaminating chemical precursors, if chemically synthesized, or substantially free of cellular material from the cell or tissue source from which they are derived. In a specific embodiment, the antigenic molecules are 60%, preferably 65%, 70%, 75%, 80%, 85%, 90%, 95%, or 99% free of contaminating chemical precursors, proteins, lipids or nucleic acids. In a preferred embodiment, the one or more antigenic molecules of a composition are substantially free of contaminating virus. Preferably, each composition for administering to a subject is at least 95%, at least 97%, or at least 99% free of contaminating virus.

In one embodiment, an antigenic molecule of a composition is a peptide having an amino acid sequence in the range of 6 to 200 amino acids, 6 to 90 amino acids, 6 to 80 amino acids, 6 to 70 amino acids, 6 to 67 amino acids, 6 to 65 amino acids, 6 to 60 amino acids, 6 to 57 amino acids, 6 to 55 amino acids, 6 to 50 amino acids, 6 to 47 amino acids, 6 to 45 amino acids, 6 to 40 amino acids, 6 to 37 amino acids, 6 to 35 amino acids, 6 to 30 amino acids, 6 to 27 amino acids, 6 to 25 amino acids, 6 to 20 amino acids, 6 to 17 amino acids, 6 to 15 amino acids, or 6 to 10 amino acids.

In another embodiment, an antigenic molecule of a composition is a protein having an amino acid sequence in the range of 200 to 2000 amino acids, or 300 to 3000 amino acids. In specific embodiments, the antigenic molecule is a protein having an amino acid sequence in the range of 200 to 1500 amino acids, 200 to 1000 amino acids, 200 to 500 amino acids, 300 to 2500 amino acids, 300 to 2000 amino acids, 300 to 1500 amino acids, 300 to 1000 amino acids, or 300 to 500 amino acids. In a preferred embodiment, the antigenic molecule is a protein having an amino acid sequence in the range of 200 to 500, 500 to 1000, 1000 to 2000, or 2000 to 3000 amino acids.

In one embodiment, an epitope of the antigenic molecule is a peptide of about 6 to 9 amino acids, 6 to 12 amino acids, 6 to 14 amino acids, 6 to 16 amino acids, 6 to 18 amino acids, 8 to 11 amino acids, or 10 to 18 amino acids. In one embodiment, an epitope of an antigenic molecule is a peptide of 6, 7, 8, 9, 10, 11, 12, 13, 14, 15, 16, 17, 18, 19, 20, 21, 22, 23, 24, 25, 26, 27, 28, 29, or 30 amino acids.

The antigenic molecules of the invention may comprise epitopes that are B cell specific or T cell specific epitopes. For example, the epitopes of the NS3 region of the dengue virus are generally T cell specific epitopes, while those of the structural glycoprotein E may bind to antibodies on the surface of B cells (see Rothman, Adv. Virus Res. 2003 60:397-419). Specific examples of T-cell epitopes on dengue viral proteins include the following epitopes, amino acid numbering according to Rothman and references therein: C (47-55); C (83-92); NS3 (71-79); NS3 (146-154); NS3 (202-211); NS3 (222-231); NS3 (224-234); NS3 (235-243); NS3 (241-249); NS3 (255-264); NS3 (351-361); NS3 (500-508); and NS3 (527-535). Examples of immunodominant peptides of another flavivirus, the Murray Valley encephalitis virus, are described by Regner et al. in J. Immunol. 2001 166:3820-28. For a description of the antigenic structure of flavivirus proteins generally, see Roehrig, Adv. Virus Res. 59:141-75.

Epitopes capable of eliciting a B cell mediated response include, for example, peptides that bind with high affinity to an antibody of a resting B cell, thereby stimulating the B cell to proliferate and secrete the high affinity antibody. For example, the hemagglutinin protein of the influenza virus comprises a number of B cell specific epitopes and the structural glycoprotein E of dengue virus may bind to antibodies secreted by B cells.

The antigenic molecules of the invention may comprise epitopes selected from epitopes known to be subdominant or dominant epitopes. Preferably, at least one epitope of an antigenic molecule is a subdominant epitope. The preferred measure of the immunodominance of an epitope is, following immunization of a subject with multiple epitopes, the relative ability of the epitope, compared to the other epitopes administered to the subject, to stimulate a cytotoxic T cell response as measured by a cytotoxic T cell assay. Examples of such assays are provided in Section 5.6. The dominance of an epitope can also be predicted based on its binding affinity to antibodies or T cell receptors. Epitopes having high affinity for antibodies or T cell receptors are expected to be more dominant than epitopes having a comparably low binding affinity for the antibodies or T cell receptors. However, other factors, such as intracellular processing of the peptide epitope, will affect whether and at what level an epitope is presented at the cell surface and consequently whether it will elicit a significant immune response. Methods for measuring and monitoring immunodominance are provided in Section 5.6.

Immunodominant epitopes and subdominant epitopes that may be used in accordance with the methods of the invention are known in the art and include, for example, those provided by the following references: van der Most et al. describe dominant and subdominant epitopes of chronic lymphocytic choriomeningitis virus in J. Immunol. 1996 157:5543-54. For example, NP (118-126) is a dominant epitope and GP (35-43), GP (99-108), and GP (283-291) are subdominant epitopes (amino acid numbering according to van der Most and references therein). Subdominant and dominant epitopes of HIV-1 are described by Lichterfeld et al. in Trends in Immunology 2005 26:166-71; Corbet et al. J. Gen. Virol. 2003 84:2409-21; Santra et al. J. Immunol. 2002 168:1847-53; and Goulder et al. J. Exp. Med. 1997 185:1423-33. Subdominate epitopes of Epstein-Barr virus ("EBV") are described by Micheletti et al. Eur. J. Immunol. 1999 29:2579-89; and Duraiswamy et al. Can. Res. 2004 64:1483-89. Examples of dominant epitopes for EBV are provided by Hollsberg in Scand. J. Immunol. 2002 55:189-95. Bertoletti et al. describe dominant and subdominant epitopes of hepatitis B virus in J. Exp. Med. 1994 180:933-43. Examples of epitopes of hepatitis C virus are provided by Himoudi et al. in J. Virology 2002 76:12735-746. Immunodominance has also been recognized in association with the influenza virus, see for example Meijers et al. J. Mol. Biol. 2005 345:1099-1110. Protection against lethal viral infection by vaccination with subdominant peptides was demonstrated by Oukka et al. in J. Immunol. 1996 157:3039-45. Sendai virus epitopes are described by Cole et al. in J. Immunol. 1997 158:4301-09 and in J. Virology 1995 69:8057-8060. Busch and Pamer describe immunodominance in the context of *Listeria monocytogenes* infections in J. Immunol. 1998 160:4441-48. Taracha et al. provide examples of immunodominance in the vaccination of cattle against *Theileria parva* in J. Immunology 1995 155: 4854-4890.

In a preferred embodiment, the epitope of an antigenic molecule elicits a T cell mediated immune response, preferably a cytotoxic T cell response, in the subject to whom it is administered according to the methods of the invention. Such epitopes are known in the art and include, for example, peptides capable of binding to major histocompatibility complex ("MHC") class I or class II molecules. Preferably, the epitopes are MHC class I binding peptides, for example, peptides that bind to MHC molecules produced by the HLA-A, HLA-B, and HLA-C human genes or the H-2, K, D, and L murine genes, or their equivalents in other species. The art contains numerous examples of MHC binding peptides and of peptides which are predicted to bind to MHC molecules because they comprise known MHC binding sequence motifs. For example, the Molecular Immunology Foundation associated with Harvard University maintains a publicly accessible database of peptides of infectious agents that bind, or are predicted to bind, to MHC molecules derived from a number of mammalian species.

In certain embodiments, the amino acid sequence variability of the epitopes of each composition administered according to the methods of the invention can be described as "epitopic variance" or "$p_{epitope}$". For example, for two epitopes the variance is calculated as the sum of the number of non-conservative ("NC") amino acid changes and one half of the number of conservative amino acid changes ("C") divided by the total number of amino acids ("T") in the epitope:

$$p_{epitope} = (NC + (0.5*C))/T.$$

For greater than two epitopes, the epitopic variance is defined as the average of this quantity over all pairs of epitopes. Conservative and non-conservative amino acid changes are known in the art. See, for example, W. R. Taylor, The Classification of Amino Acid Conservation, J. Theor. Biol. 1986 119:205-218, and D. Bordo and P. Argos, Suggestions for "Safe" Residue Substitutions in Site-Directed Mutagensis, 1991 J. Mol. Biol. 217:721-729. Generally, a conservative amino acid change refers to a substitution of one amino acid for another amino acid having substantially similar chemical properties, specifically with reference to the amino acid side chains. A non-conservative change refers to a substitution of one amino acid for another amino acid having substantially different chemical properties. Generally, conservative substitutions are those recognized in the art as being unlikely to affect the overall structure or biological function of the polypeptide, while non-conservative changes are recognized as more likely to affect structure and function.

Non-limiting examples of a conservative amino change include substitution of amino acids within the following groups: aliphatic, aromatic, polar, nonpolar, acidic, basic, phosphorylatable hydrophobic, hydrophilic, small nonpolar, small polar, large nonpolar, and large polar. Non-limiting examples of non-conservative amino acid changes include substitutions of amino acids between any of the foregoing groups.

In one embodiment, a conservative amino acid change is a substitution in which the substitution matrix for the pair of residues has a positive value. Examples of amino acid substitution matrices are known in the art, for example the BLOSUM50 matrix or the PAM250 matrix (see W. A. Pearson, Rapid and Sensitive Sequence Comparison with FASTP and FASTA, Meth. Enzymology, 1990 183:63-98, ed. R. Doolittle, Academic Press, San Diego). For further examples of scoring matrices and a comparison between them see M. S.

Johnson and J. P. Overington, 1993, A Structural Basis for Sequence Comparisons: An Evaluation of Scoring Methodologies, J. Mol. Biol. 233:716-738.

In a preferred embodiment, a conservative amino acid change is a substitution of one amino acid for another amino acid within the same chemical group wherein the groups are selected from neutral and polar amino acids (Ser, Thr, Pro, Ala, Gly, Asn, Gln), negatively charged and polar amino acids (Asp, Glu), positively charged and polar amino acids (His, Arg, Lys), nonpolar amino acids lacking a ring structure (Met, Ile, Leu, Val), nonpolar amino acids having a ring structure (Phe, Tyr, Trp), and Cysteine.

It is envisioned that the methods of the invention will be useful regardless of the specific epitopic variances among the epitopes of the antigenic molecules. However, in certain embodiments, the epitopic variance may be predictive of the relative ability of two or more compositions to elicit an immune response. In one embodiment, the epitopic variance refers to the variance between a dominant epitope and one or more subdominant epitopes. In one embodiment, the epitopic variance is a value between zero ("0") and 1. In one embodiment, the epitopic variance is from 0.01 to 0.10, from 0.01 to 0.20, from 0.01 to 0.30, from 0.01 to 0.40, from 0.01 to 0.50, from 0.01 to 0.60, from 0.01 to 0.70, from 0.01 to 0.80, or from 0.01 or 0.90. In another embodiment, the epitopic variance is from 0.10 to 0.80, from 0.10 to 0.70, from 0.10 to 0.60, from 0.10 to 0.50, or from 0.10 to 0.40. In a preferred embodiment, the epitopic variance is from 0.02 to 0.50, from 0.02 to 0.40, from 0.10 to 0.50, or from 0.10 to 0.40.

Specific non-limiting examples of dominant and subdominant epitopes, along with their calculated epitopic variances, are provided in Table 1; additional examples of calculated epitopic variance values are provided in Table 2; and examples of epitopes for common infectious agents are provided in Table 3.

TABLE 1

Examples of Dominant and Subdominant Epitopes and Epitopic Variances

| Pathogen | Dominant | Subdominant | P$_{epitope}$ (ratio) | P$_{epitope}$ | Sequence ID | Reference |
|---|---|---|---|---|---|---|
| Adenovirus | YLLEMLWRL | YLQQNWTL | (1 + 0.5 + 1 + 1 + 1)/9 | 0.39 | SEQ ID NO: 1 | Cancer Res. (2004) 64, 1483-89 |
| Dengue | TPEGIIPAL | TPEGIIPSM | 1.0/9 | 0.11 | SEQ ID NO: 2 | J. Exp. Med. (1995) 182:853-63 |
| Dengue | TPEGIIPAL | TPEGIIPTL | 0.5/9 | 0.06 | SEQ ID NO: 3 | J. Exp. Med. (1995) 182:853-63 |
| Epstein Barr virus | CLAGLLTMV | CLGGLLTMV | 0.5/9 | 0.06 | SEQ ID NO: 4 | Eur. J. Immunol. (1999) 29:2579-89 |
| Epstein Barr virus | GLCTIVAML | LLWTLVLL | (1 + 1 + 1 + 0.5)/9 | 0.39 | SEQ ID NO: 5 | Scand. J. Immunol. (2002) 55, 189-195 |
| Epstein Barr virus | IVTDFSVIK | AVFDRKSDAK | (1 + 1 + 1 + 1 + 1 + 1 + 1)/9 = 7/9 | 0.78 | SEQ ID NO: 6 | Annu. Rev. Immunol. (1997) 15:405-31 |
| Epstein Barr virus | QAKWRLQTL | FLRGRAYGL | (1 + 1 + 1 + 0.5 + 1 + 1 + 1 + 0.5) = 6/9 | 0.67 | SEQ ID NO: 7 | Annu. Rev. Immunol. (1997) 15:405-31 |
| Epstein Barr virus | YLAGLLTMV | CLGGLLTMV | (1 + 0.5)/9 | 0.17 | SEQ ID NO: 8 | Eur. J. Immunol. (1999) 29:2579-89 |
| Flaviviridae | EEHSGNEI | REHRKVAI | (1 + 1 + 1 + 1 + 1)/8 | 0.63 | SEQ ID NO: 9 | J. Immunol. (2001), 166:3820-28 |
| Flaviviridae | EEHSGNEI | TEHSGNEI | 1/8 | 0.13 | SEQ ID NO: 10 | J. Immunol. (2001), 166:3820-28 |
| Flaviviridae | EEHSGNEI | AEHTGREI | (1 + 0.5 + 1)/8 | 0.31 | SEQ ID NO: 11 | J. Immunol. (2001), 166:3820-28 |
| Flaviviridae | EEHSGNEI | EEHDGNEI | 1/8 | 0.13 | SEQ ID NO: 12 | J. Immunol. (2001), 166:3820-28 |
| Hepatitis B-virus | FLPSDFFPSV | FLPNDFFPSV | 1/10 | 0.10 | SEQ ID NO: 13 | J. Exp. Med. (1994) 933-43 |
| Hepatitis B virus | FLPSDFFPSV | FLPNDFFPSA | 2/10 | 0.20 | SEQ ID NO: 14 | J. Exp. Med. (1994) 933-43 |
| Hepatitis B virus | FLPSDFFPSV | FLPVDFFPSV | 1/10 | 0.10 | SEQ ID NO: 15 | J. Exp. Med. (1994) 933-43 |

TABLE 1-continued

Examples of Dominant and Subdominant Epitopes and Epitopic Variances

| Pathogen | Dominant | Subdominant | $P_{epitope}$(ratio) | $P_{epitope}$ | Sequence ID | Reference |
|---|---|---|---|---|---|---|
| Hepatitis B virus | FLPSDFFPSV | FLPADFFPSV | 0.5/10 | 0.05 | SEQ ID NO: 16 | J. Exp. Med. (1994) 933-43 |
| Hepatitis B virus | FLPSDFFPSV | FLPADFFPSI | (0.5 + 0.5)/10 | 0.10 | SEQ ID NO: 17 | J. Exp. Med. (1994) 933-43 |
| Hepatitis C virus | DLMGYIPLV | ILDSFDPLR | (1 + 1 + 0.5 + 0.5 + 1 + 1)/9 = 5/9 | 0.56 | SEQ ID NO: 18 | J. Virology (2002), 76, 12735-46 |
| HIV | GLADQLIHL | GLADQLIHM | 0.5/9 | 0.06 | SEQ ID NO: 19 | J. General Virology (2003) 84:2409-21 |
| HIV | NVWATHACY | NIWATHACV | 0.5/9 | 0.06 | SEQ ID NO: 20 | J. General Virology (2003) 84:2409-21 |
| HIV | RLRPGGKKK | RLRPGGKKC | 1/9 | 0.11 | SEQ ID NO: 21 | J. Exp. Med. (1997), 185, 1423-33 |
| HIV | SLVKHHMYV | SLVKHHMYI | 0.5/9 | 0.06 | SEQ ID NO: 22 | J. General Virology (2003) 84:2409-21 |
| HIV | SLYNTVATL | SLFNTVATL | 0.5/9 | 0.06 | SEQ ID NO: 23 | J. Exp. Med. (1997), 185, 1423-33 |
| Influenza A | ASNENMETM | SSLENFRAYV | (0.5 + 1 + 1 + 1 + 1 + 1 + 0.5)/9 = 5/9 | 0.56 | SEQ ID NO: 24 | J. Mol. Biol. (2005) 345, 1099-110 |
| Influenza A/PR8/34 | ASNENMETM | ASNENMDAM | (0.5 + 0.5)/9 | 0.11 | SEQ ID NO: 25 | J. Immunol. (1996) 157:3039-45 |
| Listeria | GYKDGNEYI | GYLTDNDEI | (1 + 1 + 1 + 0.5 + 1)/9 | 0.50 | SEQ ID NO: 26 | J. Immunol. (1998) 160:4441-48 |
| Listeria | KYGVSVQDI | IYVGNGQMI | (1 + 1 + 1 + 1 + 1 + 1)/9 | 0.67 | SEQ ID NO: 27 | J. Immunol. (1998) 160:4441-48 |
| Simian Immunodeficiency virus | CTPYDINQM | STPPLVRLV | (1 + 1 + 1 + 0.5 + 1 + 1 + 0.5)/9 = 6/9 | 0.67 | SEQ ID NO: 28 | J. Immunol. (2002) 168:1847-53 |

TABLE 2

Examples of p-epitope values calculated for peptides used in studies of cytotoxic T cell vaccines.*

| | TYQRTRALV | SYIPSAEKI | YPHFMPTNL | RPQASGVYM | SDYEGRLI | EEGAIVGEI | ASNENMDAM | SGPSNTPPEI | SIINFEKL | FAPGNYPAL |
|---|---|---|---|---|---|---|---|---|---|---|
| TYQRTRALV SEQ ID. NO: 29 | 0 | 0.7222 | 0.8889 | 0.7778 | 0.6875 | 0.8889 | 0.8333 | 0.7222 | 0.8125 | 0.8889 |
| SYIPSAEKI SEQ ID. NO: 30 | 0.7222 | 0 | 0.8889 | 0.7222 | 0.8125 | 0.8333 | 0.8333 | 0.7222 | 0.5625 | 0.8889 |
| YPHFMPTNL SEQ ID. NO: 31 | 0.8889 | 0.8889 | 0 | 0.7778 | 0.75 | 0.7778 | 0.8889 | 0.6111 | 0.8125 | 0.7222 |
| RPQASGVYM SEQ ID. NO: 32 | 0.7778 | 0.7222 | 0.7778 | 0 | 0.6875 | 0.8333 | 0.7778 | 0.7222 | 0.875 | 0.8333 |
| SDYEGRLI SEQ ID. NO: 33 | 0.6875 | 0.8125 | 0.75 | 0.6875 | 0 | 0.875 | 0.6875 | 0.75 | 0.75 | 0.8125 |
| EEGAIVGEI SEQ ID NO: 34 | 0.8889 | 0.8333 | 0.7778 | 0.8333 | 0.875 | 0 | 0.8889 | 0.6667 | 0.9375 | 0.7778 |
| ASNENMDAM SEQ ID. NO: 35 | 0.8333 | 0.8333 | 0.8889 | 0.7778 | 0.6875 | 0.8889 | 0 | 0.7222 | 0.625 | 0.6667 |
| SGPSNTPPEI SEQ ID. NO: 36 | 0.7222 | 0.7222 | 0.6111 | 0.7222 | 0.75 | 0.6667 | 0.7222 | 0 | 0.8125 | 0.5 |
| SIINFEKL SEQ ID. NO: 37 | 0.8125 | 0.5625 | 0.8125 | 0.875 | 0.75 | 0.9375 | 0.625 | 0.8125 | 0 | 0.625 |
| FAPGNYPAL SEQ ID NO: 38 | 0.8889 | 0.8889 | 0.7222 | 0.8333 | 0.8125 | 0.7778 | 0.6667 | 0.5 | 0.625 | 0 |

*See Elliott, S.L. et al., 1999 Vaccine 17:2009-2019.

TABLE 3

Examples of epitopes for some infectious agents*.

| Pathogen | Sequence | Sequence ID: |
|---|---|---|
| Dengue: | TPEGIIPAL | SEQUENCE ID: 39 |
| Dengue: | TPEGIIPSM | SEQUENCE ID: 40 |
| Dengue: | TPEGIIPTL | SEQUENCE ID: 41 |
| Dengue: | GTSGSPIIDKK | SEQUENCE ID: 42 |
| Dengue: | GTSGSPIVDRK | SEQUENCE ID: 43 |
| Dengue: | GTSGSPIVDKK | SEQUENCE ID: 44 |
| Dengue: | GTSGSPIADKK | SEQUENCE ID: 45 |
| Dengue: | GTSGSPIVNRE | SEQUENCE ID: 46 |
| Dengue: | GTSGSPIINRE | SEQUENCE ID: 47 |
| Dengue: | GTSGSPIINRK | SEQUENCE ID: 48 |
| Dengue: | LAPTRVVAAEME | SEQUENCE ID: 49 |
| Dengue: | LAPTRVVASEMA | SEQUENCE ID: 50 |
| Dengue: | DSGCVVSWKNKELKC | SEQUENCE ID: 51 |
| Dengue: | DSGVINWKGRELKC | SEQUENCE ID: 52 |
| Dengue: | DMGCVINWKGKELKC | SEQUENCE ID: 53 |
| Dengue: | DMGCVVSWSGKELKC | SEQUENCE ID: 54 |
| Dengue: | GYISTRVEM | SEQUENCE ID: 55 |
| Dengue: | GYISTRVGM | SEQUENCE ID: 56 |
| Kunji: | GYISTRVEL | SEQUENCE ID: 57 |
| Murray Valley Encephalitis: | GYIATRVEA | SEQUENCE ID: 58 |
| West Nile Virus: | GYIATKVEL | SEQUENCE ID: 59 |
| Japanese Encephalitis: | GYIATKVEL | SEQUENCE ID: 60 |
| Yellow Fever: | GWAAHRARA | SEQUENCE ID: 61 |
| HIV: | GLADQLIHL | SEQUENCE ID: 62 |
| HIV: | GLADQLIHM | SEQUENCE ID: 63 |
| HIV: | SLVKHHMYV | SEQUENCE ID: 64 |
| HIV: | SLVKHHMYI | SEQUENCE ID: 65 |
| HIV: | NVWATHACV | SEQUENCE ID: 66 |
| HIV: | NIWATHACV | SEQUENCE ID: 67 |
| HIV: | SLYNTVATL | SEQUENCE ID: 68 |
| HIV: | SLFNTVATL | SEQUENCE ID: 69 |
| HIV: | RLRPGGKKK | SEQUENCE ID: 70 |
| HIV: | RLRPGGKKC | SEQUENCE ID: 71 |

TABLE 3-continued

Examples of epitopes for some infectious agents*.

| Pathogen | Sequence | Sequence ID: |
|---|---|---|
| HIV-2: | TPYDINQML | SEQUENCE ID: 72 |
| HIV-1: | TPQDLNMML | SEQUENCE ID: 73 |
| HIV-2: | TSTVEEQIQW | SEQUENCE ID: 74 |
| HIV-1: | TSTLQEQIGW | SEQUENCE ID: 75 |
| HIV-1: | ALTDICTEM | SEQUENCE ID: 76 |
| HIV-1: | ALVEICTEM | SEQUENCE ID: 77 |
| HIV-1: | ALTAICEEM | SEQUENCE ID: 78 |
| HIV-1: | ALIEICSEM | SEQUENCE ID: 79 |
| HIV-1: | KMIGGIGGFI | SEQUENCE ID: 80 |
| HIV-1: | KVIVGIGGFI | SEQUENCE ID: 81 |
| HIV-1: | VLVGPTPVNI | SEQUENCE ID: 82 |
| HIV-1: | VLVGPTPTNV | SEQUENCE ID: 83 |
| HIV-1: | VLAEAMSQV | SEQUENCE ID: 84 |
| HIV-1: | VLAEAMSQA | SEQUENCE ID: 85 |
| HIV-1: | VLAEAMSQI | SEQUENCE ID: 86 |
| HIV-1: | KLTPLCVTL | SEQUENCE ID: 87 |
| HIV-1: | KLTPLCVPL | SEQUENCE ID: 88 |
| Influenza: | ASNENMETM | SEQUENCE ID: 89 |
| Influenza: | SSLENFRAYV | SEQUENCE ID: 90 |
| Influenza: | ASNENMETM | SEQUENCE ID: 91 |
| Influenza: | ASNENMDAM | SEQUENCE ID: 92 |
| Influenza: | SFYRNVVWLIKK | SEQUENCE ID: 93 |
| Influenza: | SFFRNVVWLIKK | SEQUENCE ID: 94 |
| Influenza: | SFLRNVVWLIKK | SEQUENCE ID: 95 |
| Influenza: | ASNENMETM | SEQUENCE ID: 96 |
| Influenza: | SSLENFRAYV | SEQUENCE ID: 97 |
| Influenza: | SSAENFRAYV | SEQUENCE ID: 98 |
| Influenza: | SSLENFAAYV | SEQUENCE ID: 99 |
| Epstein-Barr Virus: | YLAGLLTMV | SEQUENCE ID: 100 |
| EBV | CLAGLLTMV | SEQUENCE ID: 101 |
| EBV: | CLGGLLTMV | SEQUENCE ID: 102 |
| EBV: | GLCTLVAML | SEQUENCE ID: 103 |
| EBV: | LLWTLVVLL | SEQUENCE ID: 104 |
| Heptatitis B Virus: | FLPSDFFPSV | SEQUENCE ID: 105 |
| HBV: | FLPNDFFPSV | SEQUENCE ID: 106 |
| HBV: | FLPNDFFPSA | SEQUENCE ID: 107 |
| HBV: | FLPVDFFPSV | SEQUENCE ID: 108 |
| HBV: | FLPADFFPSV | SEQUENCE ID: 109 |
| HBV: | FLPADFFPSI | SEQUENCE ID: 110 |

*Additional information regarding the epitopes listed in this table can be found in the following references: Zivny, et al., J. Exp. Med. 182, 853 C863 (1995); Mongkolsapaya, Nat. Med., 9(7):921-7 (2003); Zivna, J. Immunol. 168:5959-5965 (2002); Huang, J. Med. Virol., 57:1-8 (1999); Spaulding, J. Virol., 73(1): 398-403 (1999); Corbet, J. of General Virology, 84, 2409-21 (2003); Goulder, J. Exp. Med., 185, 1423-1433 (1997); Gillespie, Eur. J. Immunol. 35(2005); Singh, J. Immunol. 173, 4387-4393 (2004); McKinney, J. Immunol. 173, 1941-1950 (2004); Meijers, J. Mol. Biol., 345, 1099-1110 (2005); Oukka, J. Imunol. 157:3039-3045 (1996); Hioe, J. Virol., 64(12), 6246-6251 (1990); Turner, Nat. Immunol., 6(4), 382-9 (2005); Micheletti, Eur. J. Immunol. 29: 2579-2589 (1999); Hollsberg, Scand. J. Immunol. 55(2): 189-95 (2002); Bertoletti, J. Exp. Med., 180(3), 933-943 (1994); and Bertoletti, Nature, 369(2) 407-410 (1994).

5.3 Infectious Diseases and Agents

The present invention comprises methods of treating or preventing an infectious disease in a subject by eliciting an immune response against one or more infectious agents which cause the disease. In one embodiment, the methods comprise treating or preventing one or more infectious diseases caused by one or more infectious agents. Infectious agents encompassed by the methods of the invention include, without limitation, viruses, bacteria, fungi, protozoa, helminths, and parasites, and particular strains thereof. The methods of the invention are particularly useful in eliciting an effective immune response against one or more infectious agents having a high rate of mutation or having multiple subtypes or "strains." As used herein, a "strain" refers to a sub-group of a given species of infectious agent that differs slightly in some of its features with respect to the other strains of the same infectious agent. The difference may be defined by the DNA sequence, by the response to a biochemical assay, by antigenicity, or by pathology in the host. Several strains of a single species of infectious agent can coexist in a population of hosts or even in a single host. Further non-limiting examples of infectious agents and strains thereof which are encompassed by the methods of the invention are provided in the sections that follow.

5.3.1 Viruses

In certain embodiments of the invention, the infectious agent is a virus, preferably a multi-strain virus. Non-limiting examples of such viruses include herpes viruses (HSV-1, HSV-2, VZV, EBV, CMV, HHV-6, HHV-8), influenza viruses (Flu A, B), hepatitis viruses (HepA, HepB, HepC, HepE), human immunodeficiency viruses (HIV-1, HIV-2), respiratory syncytial viruses, measles viruses, rhinoviruses, adenoviruses, SARS viruses, papillomaviruses, orthopoxviruses, West Nile viruses, and a dengue viruses. In one embodiment, the virus is a member of the Flaviviridae family of viruses. In a preferred embodiment, the virus is a flavivirus selected from the group consisting of dengue, Kunjin, Japanese encephalitits, West Nile, and yellow fever virus.

In one embodiment, the virus is one that is known to escape immune surveillance by mutation of immunodominant T cell epitopes. Non-limiting examples of such viruses include lymphocytic choriomenignitis virus, hepatitis B virus, Epstein Barr virus, and human immunodeficiency virus.

Other examples of viruses encompassed by the methods of the invention include, without limitation, the following viruses: Retroviridae (e.g. human immunodeficiency viruses, such as HIV-1, also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola-like viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arenaviridae (hemorrhagic fever viruses); Reoviridae (e.g. reoviruses, orbiviurses and rotaviruses); Bomaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2), varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis, thought to be a defective satellite of hepatitis B virus), the agents of non-A, non-B hepatitis (class 1, internally transmitted; class 2, parenterally transmitted, i.e., Hepatitis C); Norwalk and related viruses, and astroviruses.

5.3.2 Bacteria

In certain embodiments of the invention, the infectious agent is a bacterium. Non-limiting examples of bacteria encompassed by the methods of the invention include *Mycobacteria, Streptococcus, Staphylococcus, Pseudomonas, Salmonella, Neisseria,* and *Listeria*. In a preferred embodiment, the bacteria is *Neisseria gonorrhea, M. tuberculosis, M. leprae, Listeria monocytogenes, Streptococcus pneumoniae, S. pyogenes, S. agalactiae, S. viridans, S. faecalis,* or *S. bovis*

Other examples of bacteria contemplated include, but are not limited to, Gram positive bacteria (e.g., *Listeria, Bacillus* such as *Bacillus anthracis, Erysipelothrix* species), Gram negative bacteria (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio,* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species.

Additional non-limiting examples of specific infectious bacteria include *Helicobacter pyloris, Borelia burgdorferi, Legionella pneumophilia, Mycobacteria avium, M. intracellulare, M. kansaii, M. gordonae, M. africanum, Staphylococcus aureus, Neisseria meningitidis, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneumoniae, Pasturella multocida, Fusobacterium nucleatum, Streptobacillus moniliformis, Treponema pallidium, Treponema pertenue, Leptospira, Rickettsia,* and *Actinomyces israelli.*

5.3.3 Parasites

Parasitic diseases that can be treated or prevented by the methods of the invention include, but are not limited to, amebiasis, malaria, leishmania, coccidia, giardiasis, cryptosporidiosis, toxoplasmosis, trypanosomiasis, schistosomiasis, and filariasis. In a preferred embodiment, the parasite is Malaria, Leishmaniases (cutaneous, visceral, and mucocutaneous leishmaniasis). *Trypanosoma cruzi,* or *Theileria parva.*

Also encompassed are infections by various worms, such as but not limited to ascariasis, ancylostomiasis, trichuriasis, strongyloidiasis, toxoccariasis, trichinosis, onchocerciasis filaria, and dirofilariasis. Also encompassed are infections by various flukes, such as but not limited to schistosomiasis, paragonimiasis, and clonorchiasis.

Further non-limiting examples of parasites include *Plasmodium* spp., *Toxoplasma gondii, Babesia* spp., *Trichinella spiralis, Entamoeba histolytica, Giardia lamblia, Enterocytozoon bieneusi, Naegleria, Acanthamoeba, Trypanosoma rhodesiense* and *Trypanosoma gambiense, Isospora* spp., *Cryptosporidium* spp, *Eimeria* spp., *Neospora* spp., *Sarcocystis* spp., and *Schistosoma* spp.

5.4 Pharmaceutical Compositions and Use

The present invention provides methods for treating or preventing an infectious disease in a subject, the methods comprising administering to the subject at least two compositions, each comprising at least one antigenic molecule having one or more epitopes of the infectious agent which causes the disease. The antigenic molecules may be polypeptides or proteins, preferably glycosylated polypeptides or proteins. The polypeptides or proteins may be purified from an organism or may be produced, for example using recombinant technology. The antigenic molecules may also comprise lipoproteins, peptidoglycans, protein-conjugated capsular polysaccharides, capsular polysaccharides, toxoids, an inactivated infectious agent, or portions the inactivated agent, such as extracts or subunits of the agent (e.g., a virus, bacterium, parasite, or protozoan)

The administering is performed such that each composition is administered to a different site of the subject. In a preferred embodiment, each site is or substantially drains to, an anatomically distinct bodily part selected from a lymph node, a group of lymph nodes, a nonencapsulated cluster of lymphoid tissue, or the spleen. In another preferred embodiment, the distance between each site is greater than the distance between any two anatomically distinct lymph nodes or groups of lymph nodes nearest each site. The same or a separate route of administration may be used for each composition. Preferably, the route of administration is chosen in order to target a composition to a particular site.

Non-limiting examples of methods of administration, formulations, effective amounts, dosages, and kits are provided by Sections 5.4.1 to 5.4.4. The present methods also encompass administering the compositions of the invention in combination with one or more therapeutic agents that aid in the prevention or treatment of infectious diseases. These embodiments, as well as specific examples of such therapeutic agents are provided by Section 5.5.

5.4.1 Methods of Administration

Any suitable route of administration is encompassed by the methods of the invention, e.g. intradermal, subcutaneous, intravenous, intramuscular, or mucosal. Mucosal routes of administration include, but are not limited to, oral, rectal, vaginal, and nasal administration. In a preferred embodiment, at least one composition is administered transdermally, intradermally, subcutaneously, orally, rectally, vaginally or by inhalation.

Preferably, the route of administration is selected to target a composition to a particular site, for example, by injection directly into a lymph node or a lymph node cluster, by oral administration to target the lymph nodes of the stomach, by anal administration to target the lymph nodes of the rectum, by inhalation or aerosol to target the lymph nodes of the lungs, or by any other suitable route of administration.

The methods of the invention provide for the administration of a plurality of compositions. In one embodiment, the number of compositions administered is in the range of 2-12, 2-10, 2-8, 2-6, 2-5, or 2-3. Preferably, the number of compositions administered is in the range of 2-5. In one embodiment, the number of compositions administered is 2, 3, 4, 5, 6, 7, 8, 9, 10, 11, or 12. In a preferred embodiment, the number of compositions administered is 2, 3, 4, or 5.

Preferably, each composition is administered at substantially the same time, for example, within one to eight hours or during the same doctor's visit. In one embodiment, each composition is administered within one to two hours, within one to three hours, within one to four hours, or within one to five hours.

In another embodiment, the methods of the invention further comprise administering at least one composition at a separate time, prior to the administration of the other compositions. For example, at least one composition is administered 3 to 14 days before the other compositions are administered. In a preferred embodiment, at least one composition is administered 6 days before the other compositions are administered. Preferably, the composition administered at an earlier time comprises one or more subdominant epitopes and at least one of the compositions administered at the later time comprises one or more dominant epitopes, and all of the compositions administered at the later time are administered together, at substantially the same time. In particular embodiments, the first composition is administered 3 days, 4 days, 5 days, 6 days, 7 days, 8 days, 9 days, 10 days, 11 days, 12 days, 13 days or 14 days before the other compositions are administered. In another embodiment, the first composition is administered 3-10 days, 4-10 days, 5-10 days, or 6-10 days before the other compositions are administered. In certain embodiments, at least one composition is administered 1 month, 2 months, 3 months, 4 months, 5 months, 6 months, 7 months, 8 months, 9 months, 10 months, 11 months, or 12 months before the other compositions are administered.

The compositions of the invention may also be administered prior to, concurrently with, or subsequent to the administration of one or more adjuvants. Adjuvants contemplated include, but are not limited to, oil-based adjuvants, CpG oligonucleotides, aluminum salt adjuvants, calcium salt adjuvants, emulsions and surfactant-based formulations. The adjuvants contemplated for administration prior to, concurrently with, or subsequent to the administration of the composition of the invention are described in more detail in Section 5.4.2 in connection with formulations. It is envisioned that the adjuvants discussed in Section 5.4.2 may optionally be administered separately from the compositions, rather than in formulation with them as described in that section.

5.4.2 Formulations

Pharmaceutical compositions comprising the compositions of the invention, and their physiologically acceptable salts and solvates, can be formulated using one or more physiologically acceptable carriers or excipients. The formulations are preferably for intradermal or subcutaneous administration, but can be for administration by other means such as by inhalation or insufflation (either through the mouth or the nose), oral, buccal, parenteral, vaginal, or rectal. Preferably, the compositions are formulated to provide increased chemical stability of the antigenic molecules during storage and transportation. For example, in one embodiment, the antigenic molecules comprise polypeptides and the formulation prevents or reduces oligomerization of the polypeptides. In another example, the formulation prevents or reduces oxidation of the amino acid residues of the polypeptides. The formulations may be lyophilized or liquid formulations.

In one embodiment, the compositions are formulated for injection. In a preferred embodiment, the compositions are sterile lyophilized formulations, substantially free of contaminating cellular material, chemicals, virus, or toxins. In a particular embodiment, formulations for injection are provided in sterile single dosage containers. The formulations may or may not contain an added preservative. Liquid formulations may take such forms as suspensions, solutions or emulsions in oily or aqueous vehicles, and may contain formulatory agents such as suspending, stabilizing and/or dispersing agents. In one embodiment, the formulation comprises liposomes.

In one embodiment, the compositions further comprise one or more adjuvants. Adjuvants may comprise any number of delivery systems, for example, mineral salts, surface active agents, synthetic microparticles, oil-in-water emulsions, immunostimulatory complexes, liposomes, virosomes, and virus-like particles. Adjuvants further comprises one or more potentiators of the immune response such as microbial derivatives (e.g., bacterial products, toxins such as cholera toxin and heat labile toxin from $E.$ $coli$, lipids, lipoproteins, nucleic acids, peptidogylcans, carbohydrates, peptides), cells, cytokines, (e.g., dendritic cells, IL-12, and GM-CSF), hormones, and small molecules. Adjuvants contemplated include, but are not limited to, oil-based adjuvants (e.g., Freund's adjuvant), CpG oligonucleotides (see Klinman 2003 Expert Rev. Vaccines 2:305-15) aluminum salt adjuvants, calcium salt adjuvants, emulsions and surfactant-based formulations (e.g., MF59, ASO2, montanide, ISA-51, ISA-720, and QA21). For a review of improvements in vaccine adjuvants, see Pashine et al. 2005, Nature Med. 11(4):S63-S68.

5.4.3 Effective Amounts and Dosages

An effective amount of the compositions of the invention is the amount sufficient to reduce the severity of an infectious disease or one or more symptoms thereof, the amount sufficient to reduce the duration of the disease, the amount sufficient to ameliorate one or more symptoms of the disease, the amount sufficient to prevent the incidence or advancement of the disease or the amount sufficient to enhance or improve the therapeutic effect(s) of another therapy or therapeutic agent.

In one embodiment, the effective amount of the compositions of the invention is the amount sufficient to produce an antibody secreting B cell or cytotoxic T cell mediated immune response directed against one or more molecules of each composition administered to a subject. The ability of the molecules of a composition to elicit an immune response can be determined using any routine method available to those of skill in the art. Non-limiting examples of such methods are provided in Section 5.6. In one embodiment, the effective amount of each composition is the amount sufficient to produce a cytotoxic T cell response in the subject as measured, for example, by a mixed lymphocyte T cell assay.

In a preferred embodiment, the effective amount of each composition is an amount sufficient to mitigate or avoid the immunodominance of an epitope of an antigenic molecule of any of the compositions.

In one embodiment, the effective amount of each composition administered at a particular site of the subject is that which delivers an amount of antigenic molecules in the range of 1 to 1000 micrograms. In a specific embodiment, the amount of antigenic molecules is in the range of 1 to 100 micrograms, 1 to 200 micrograms, 1 to 300 micrograms, 1 to 400 micrograms, 1 to 500 micrograms, 1 to 600 micrograms, 1 to 700 micrograms, 1 to 800 micrograms, or 1 to 900 micrograms. In another specific embodiment, the amount of antigenic molecules is in the range of 1 to 10 micrograms, 1 to 20 micrograms, 1 to 30 micrograms, 1 to 40 micrograms, 1 to 50 micrograms, 1 to 60 micrograms, 1 to 70 micrograms, 1 to 80 micrograms, or 1 to 90 micrograms. Each composition may comprise the same or a different amount of antigenic molecules. In a preferred embodiment, the amount of antigenic molecules of a composition comprising dominant epitopes is less than that of the other compositions. Preferably, the total amount of antigenic molecules administered to a subject does not exceed 5 milligrams, and most preferably the total amount does not exceed 2 milligrams, where the administering of each composition is at substantially the same time.

5.4.4 Kits

The invention provides a pharmaceutical pack or kit for carrying out the methods or therapeutic regimens of the invention. In one embodiment, the kit comprises in separate containers at least two compositions, each composition comprising one or more epitopes of an infectious agent or strain thereof. In another embodiment, each composition comprises at least one purified antigenic molecule, and each purified antigenic molecule comprising one or more epitopes of one or more infectious agents or strains thereof, the epitopes having an epitopic variance of between 0.05 and 0.50.

In another embodiment, the kit further comprises in one or more additional containers an anti-viral agent, an anti-bacterial agent, a cytokine, or an adjuvant.

The composition in each container may be in the form of a pharmaceutically acceptable solution, e.g., in combination with sterile saline, dextrose solution, or buffered solution, or other pharmaceutically acceptable sterile fluid. Alternatively, the composition may be lyophilized or desiccated; in this instance, the kit optionally further comprises in a separate container a pharmaceutically acceptable solution (e.g., saline, dextrose solution, etc.), preferably sterile, to reconstitute the composition to form a solution for injection purposes.

In another embodiment, the kit further comprises one or more reusable or disposable device(s) for administration (e.g, syringes, needles, dispensing pens), preferably packaged in sterile form, and/or a packaged alcohol pad. Instructions are optionally included for administration of the compositions by a clinician or by the patient. The kit may also comprise other materials, e.g., metal or plastic foil, such as a blister pack.

5.5 Combination Therapy

In certain embodiments, the compositions of the invention are administered in combination with one or more therapeutic agents that aid in the prevention or treatment of infectious diseases. In a particular embodiment, the agent is an antigen presenting cell, a cytokine, an antibiotic, an antiviral compound, an antiprotozoal compound, an antifungal compound, or an antihelminthic compound.

In one embodiment, the infectious disease is caused by the dengue virus and the compositions of the invention are administered in combination with one or more antisense nucleic acids which suppress or inhibit the expression of one or more dengue genes. The nucleic acids may be deoxyribonucleic acids or ribonucleic acids, or a combination thereof.

In one embodiment, the infectious disease is Lassa Fever and the compositions of the invention are administered in combination with ribavirin.

In one embodiment, the infectious disease is caused by a herpes virus and the compositions of the invention are administered in combination with one or more antiviral agents selected from the group consisting of acyclovir, brivudin, cidofovir, famciclovir, foscarnet, ganciclovir, idoxuridine, trifluridine, valaciclovir, and vidarabine.

In one embodiment, the infectious disease is caused by a hepatitis B or C virus and the compositions of the invention are administered in combination with one or more antiviral agents selected from the group consisting of interferon, adefovir dipivoxil, and lamivudine.

In one embodiment, the infectious disease is caused by a hepatitis B virus and the compositions of the invention are administered in combination with one or more antiviral agents selected from the group consisting of acyclovir, famciclovir, and ganciclovir.

In one embodiment, the infectious disease is caused by a rhinovirus and the compositions of the invention are administered in combination with one or more antiviral agents selected from the group consisting of pirodavir and pleconaril.

In one embodiment, the compositions of the invention are administered along with antigen presenting cells ("APCs") which have been sensitized according to art-recognized methods with one or more antigenic molecules of a composition. In accordance with this embodiment, the antigenic molecule-pulsed APCs serve as adjuvants for vaccination as described, for example, by Martin-Fontecha et al. 2003 J. Exp. Med. 198, 615-621. APCs, including but not limited to macrophages, dendritic cells and B-cells, can be obtained by any of various methods known in the art. Preferably, the APCs are obtained by production in vitro from stem and progenitor cells from human peripheral blood or bone marrow and most preferably the APCs are obtained from the subject or are autologous to the subject.

In one embodiment, the compositions of the invention comprise APCs sensitized with one or more antigenic molecules of an infectious agent. In another embodiment, the compositions of the invention are administered at substantially the same time as APCs sensitized with one or more antigenic molecules of a composition. In another embodiment, the APCs are administered prior to the compositions of the invention. The APCs are preferably administered at the same site as the composition comprising the antigenic molecules with which the APCs were sensitized.

5.5.1 Cytokines

The compositions of the invention may optionally be administered in combination with one or more cytokines. In one embodiment, the compositions of the invention comprise one or more cytokines. In a preferred embodiment, at least one cytokine is an interleukin or an interferon. In a particular embodiment, at least one cytokine is an interleukin selected from the group consisting of IL-1α, IL-1β, IL-2, IL-3, IL-4, IL-5, IL-6, IL-7, IL-8, IL-9, IL-10, IL-11, IL-12, IL-15, and IL-18. In another particular embodiment, at least one cytokine is an interferon selected from IFNα, IFNβ, and IFNγ.

5.5.2 Antiviral Agents

Antiviral agents that can be used in combination with the compositions of the invention include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In one embodiment, the antiviral agent is a non-nucleoside reverse transcriptase inhibitor selected from the group consisting of delavirdine, efavirenz, and nevirapine. In one embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In one embodiment, the antiviral agent is a protease inhibitor selected from the group consisting of amprenavir, atazanavir, fosamprenav, indinavir, lopinavir, nelfinavir, ritonavir, and saquinavir. In one embodiment, the antiviral agent is a fusion inhibitor such as enfuvirtide.

Additional, non-limiting examples of antiviral agents for use in combination with the methods of the invention include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; pyridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

5.5.3 Antibacterial Agents

Antibacterial agents, including antibiotics, that can be used in combination with the compositions of the invention include, but are not limited, to aminoglycoside antibiotics, glycopeptides, amphenicol antibiotics, ansamycin antibiotics, cephalosporins, cephamycins oxazolidinones, penicillins, quinolones, streptogamins, tetracyclins, and analogs thereof.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin.

In one embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim Additional, non-limiting examples of antibacterial agents for use in combination with the methods of the invention include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithromycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

5.5.4 Antiprotozoal and Antiparasitic Agents

Many examples of agents that can be used in combination with the compositions of the invention to treat protozoal or parasitic diseases are known in the art and include, but are not limited to, quinines, chloroquine, mefloquine, proguanil, pyrimethamine, metronidazole, diloxanide furoate, tinidazole, amphotericin, sodium stibogluconate, trimoxazole, and pentamidine isetionate. Specific non-limiting examples include mebendazole, levamisole, niclosamide, praziquantel, albendazole, ivermectin, diethylcarbamazine, thiabendazole, acedapsone, amodiaquine hydrochloride, amquinate, arteflene, chloroquine, chloroquine hydrochloride, chloroquine phosphate, cycloguanil pamoate, enpiroline phosphate, halofantrirrie hydrochloride, hydroxychloroquine sulfate, mefloquine hydrochloride, menoctone, mirincamycin hydrochloride, primaquine phosphate, pyrimethamine, quinine sulfate, and tebuquine.

5.6 Methods of Measuring and Monitoring Immunodominance

The methods of the present invention are particularly useful for mitigating the effects of immunodominance in the context of therapeutic or prophylactic vaccination against one or more infectious diseases. The efficacy of the therapeutic or prophylactic methods described herein may vary depending on such factors as the epitopes of the molecules comprising the compositions to be administered, the sites chosen for administration, the time of administration, and the particular infectious agent to be targeted. Accordingly, the present invention also provides methods for determining whether a vaccine composition suppresses immunodominance in a subject so that the methods may be optimized for a particular subject, population of subjects, or for one or more infectious diseases. These methods can also be used to monitor the efficacy of therapeutic or prophylactic vaccination in a subject or in a population of subjects.

The methods for measuring and monitoring immunodominance in a subject comprise administering to the subject a plurality of compositions, each composition being administered to a different site of the subject according to the methods of the invention and each composition comprising at least one antigenic molecule as described herein, and measuring an immune response to the antigenic molecule or molecules of each composition so administered. Immunodominance has been suppressed in the subject if the ratio between the immune response of the most immunogenic composition and the least immunogenic composition is reduced compared to the ratio obtained with administration of all of the compositions at a single site. In one embodiment, the ratio is reduced by 10%-20%, 20-30%, 30-40%, 40-50%, 50-60%, 60-70%, 70-80%, 80-90% or 90-100%. In another embodiment, the ratio is reduced by about 20%, about 40%, about 60%, about 80%, about 85%, about 90%, or about 95%. In a preferred embodiment, the ratio is reduced by about 50-99%.

Any routine assay for measuring an immune response to an antigenic molecule may be used in accordance with this embodiment. Preferably, the assay determines a cytotoxic T cell response to the antigenic molecules of each composition. In a preferred embodiment, the cytotoxic T cell response is determined by a tetramer assay or by measuring the cytokine profiles of responding cells, for example using and ELISPOT assay or an intracellular cytokine staining assay. In another embodiment, the response is measured by assaying the ability of T cells obtained from the subject to specifically lyse a population of target cells expressing or coated with the antigenic molecules of each composition administered to the subject. Non-limiting examples of methods for measuring the immune response elicited against the antigenic molecules of each composition are provided below for purposes of illustration only, and are not intended to limit the kinds of assays for measuring an immune response which may be used in the methods of the invention. For a summary assays useful for T cell responses see Robinson and Amara, 2005 Nature Med. 11(4):S25-32, and references infra.

5.6.1 Tetramer Staining Assay

The ability of the compositions administered according to the methods of the invention to elicit a cellular immune response, e.g., a CD4+ or a CD8+ T cell response, is preferably measured with a tetramer staining assay. This assay identifies antigen-specific T cells (see Altman et al., 1996, Science 274: 94-96; Savage et al., 2002 Br. J. Cancer 86:1336-42; Choi et al., 2003 J. Immunol. 171:5116-23). For example, tetramers are produced by multimerizing a MHC molecules complexed with the antigenic molecules, and labeled, for example, by complexing to streptavidin or a fluorescent molecule. The labeled tetramer solution is then mixed with a population of lymphocytes or peripheral blood mononuclear cells obtained from a subject treated according to the methods of the invention. T cells can be identified, for example, by labeling with anti-CD8+ fluorescent antibodies. The population of cells that are both CD8+ and which bind to the labeled tetramers can be detected, for example, by dual color flow cytometry.

5.6.2 The MLTC or Chromium Release Assay

An immune response elicited according to the methods of the invention can also be measured with a conventional mixed lymphocyte T cell assay, also referred to as a $^{51}$Cr release assay, using cells which have been pulsed with the antigenic molecule or molecules of the compositions as lysis targets. Briefly, the compositions of the invention are administered to a mammalian subject such as a mouse according to the methods described herein. Appropriate negative controls include, for example, administration of the same compositions at a single site, instead of at multiple sites, or administration of the compositions without antigenic molecule or molecules (e.g., a sham vaccination). Following a period of time after the administration of the compositions, the spleens of the vaccinated animals are removed and the lymphocytes are cultured in vitro according to routine methods. To measure the primary response, the period of time is generally from 3 to 12 days, preferably 4, 8, or 10 days for a mouse. To measure the secondary, e.g, memory, response, a longer time period is used, for example 30 days, 45 days, or 60 days. The cultured lymphocytes may optionally be re-stimulated in vitro by the addition of the antigenic molecule or molecules of the compositions that were administered. It may be desirable to include an amount of secondary mixed lymphocyte culture supernatant in the culture medium as a source of T cell growth factors (See, Glasebrook, et al., 1980, J. Exp. Med. 151:876). For example, the culture medium may comprise 30-40% of such supernatant.

After culturing in vitro for a period of time, usually from 3 to 7 days, the lymphocytes are tested for their ability to specifically lyse target cells coated with or expressing the antigenic molecule or molecules of the compositions that were administered. Specific lysis is measured, for example, with a $^{51}$Cr-release assay (see Palladino, et al., 1987, Cancer Res. 47:5074-5079 and Blachere et al., 1993, J. Immunotherapy 14:352-356). In this assay, the mixed lymphocyte culture is added to labeled target cells. The target cells are pre-labeled with the radioactive isotope by incubating the cells in culture medium containing the isotope. Typically, a number of different ratios of effector cells to target cells is used, e.g., in the range of 1:1 to 40:1. Lysis is measured as a function of $^{51}$Cr-release. Each assay point comprises an effector cell to target cell ratio, typically performed in triplicate. Appropriate positive and negative controls for $^{51}$Cr-release are, for example, target cells alone to measure spontaneous $^{51}$Cr-release, and cells lysed with detergent to measure 100% release. The amount of $^{51}$Cr released into the supernatant is measured by routine methods, for example by a gamma counter. Specific lysis is measured as the radioactivity, e.g., in counts per minute, or "cpm," in the test sample minus radioactivity in the negative control (spontaneously released) divided by the radioactivity in the positive control (total detergent released) less the negative control. Optionally, in order to block the MHC class I cascade a concentrated hybridoma supernatant derived from K-44 hybridoma cells (an anti-MHC class I hybridoma) is added to the test samples to a final concentration of 12.5%.

5.6.3 CD4+ or CD8+ T Cell Proliferation Assay

The ability of the compositions administered according to the methods of the invention to elicit a cellular immune response can also be measured as the ability to promote CD4+ or CD8+ T cell proliferation in vitro following exposure of peripheral blood mononuclear cells to the antigenic molecule or molecules of the compositions with which a subject has been vaccinated according to the methods of the invention. Primary cells are obtained from spleen, fresh blood, or CSF and purified using routine methods; for example, as described by Kruse and Sebald, 1992, EMBO J. 11: 3237 3244. The cells are incubated for a period of time, e.g., 5-12 days, with the antigenic molecule or molecules, optionally with added adjuvant or antigen presenting cells which may be added to the culture 24 to 48 hours prior to the assay. The proliferation of the cells is then measured using any of the numerous art-recognized methods for measuring cell proliferation. For example, proliferation can be measured by radiometric assays such as tritiated thymidine incorporation, by colorimetric assays such as the MTT assay, or by fluorescence assays such as those utilizing fluorescently labeled nucleotides. In another example, proliferation is measured using the carboxyl fluorescein diacetate succinimidyl (CFSE) assay which utilizes flow cytometry for detection of proliferation and cell type.

5.6.4 Antibody Response Assay

The ability of the compositions administered according to the methods of the invention to elicit a cellular immune response can also be determined by measuring antibodies produced in response to vaccination with the compositions.

For example, plates are coated with the antigenic molecule or molecules which comprise the compositions used in the vaccine and incubated with plasma or CSF from a vaccinated subject (such as a model mouse or a human patient). The presence of antibodies which have bound to the antigenic molecule or molecules is detected using routing methods, for example by incubation with a secondary antibody such as a sheep anti-mouse or anti-human immunoglobulin, as appropriate, conjugated with a detectable label or an enzyme such as horseradish peroxidase. The amount of secondary antibody which specifically binds to the plates is determined using a method appropriate for the detection of the label or the presence of the conjugated enzyme.

5.6.5 Cytokine Detection Assay

The ability of the compositions administered according to the methods of the invention to elicit a cellular immune response can also be determined indirectly, through the detection of cytokines known to be produced by activated T cells, for example, using an intracellular cytokine staining assay. Thus, the CD4+ and CD8+ T cell response can be measured by detection and quantitation of the levels of specific cytokines. For example, intracellular cytokines can be measured using an IFN-gamma detection assay. In this method, peripheral blood mononuclear cells from a subject treated according to the methods described herein are stimulated with the antigenic molecule or molecules of the compositions administered to the subject. T cells are identified by incubating the cells with T cell-specific labeled antibodies. Similarly, IFN-gamma is detected by incubating the cells with labeled antibodies reactive with IFN-gamma. The labeled cells are detected and quantitated, for example, by flow cytometry.

Alternatively, a filter immunoassay, such as the enzyme-linked immunospot assay (ELISPOT) assay, can be used to detect specific cytokines surrounding a T cell. For example, a nitrocellulose-backed microtiter plate is coated with a purified cytokine-specific primary antibody, i.e., anti-IFN-gamma, and the plate is blocked to avoid background due to nonspecific binding of other proteins. A sample of mononuclear blood cells obtained from a subject treated according to the methods of the invention is diluted onto the wells of the microtitre plate. A labeled secondary anti-cytokine antibody is added and detected using means appropriate for the particular label. Cytokine-secreting cells appear as "spots" which can be quantitated by visual, microscopic, or electronic detection methods.

6. EXAMPLE

Figure 2A:
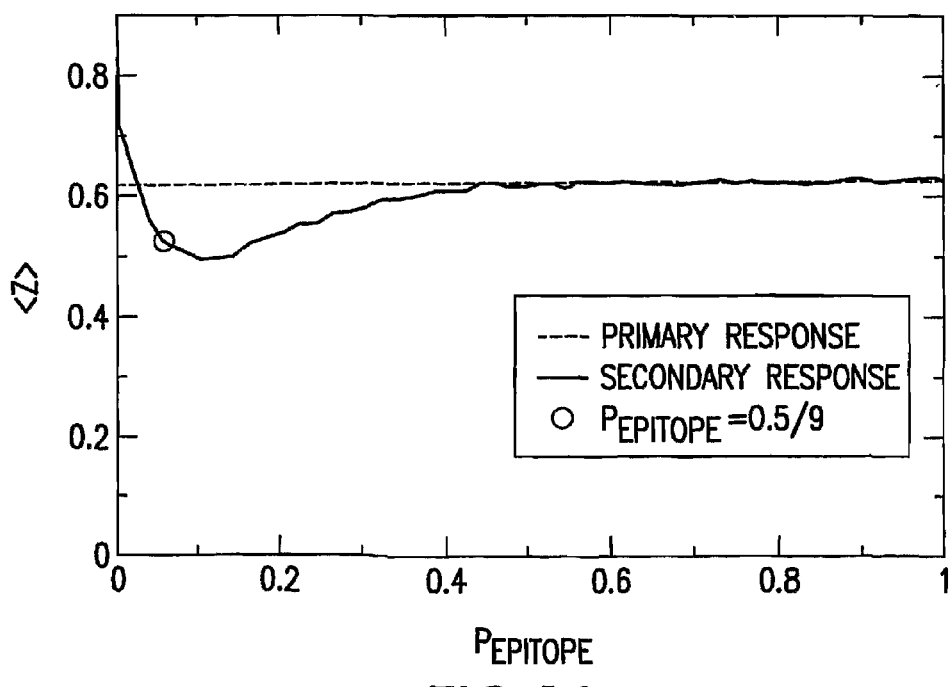
Figure 2B:
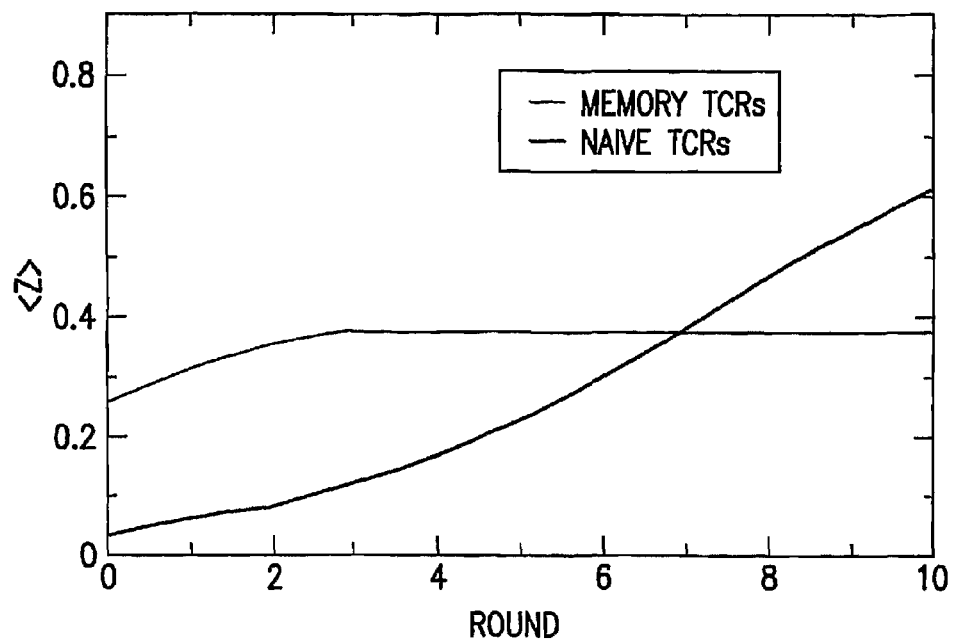
Figure 2C:
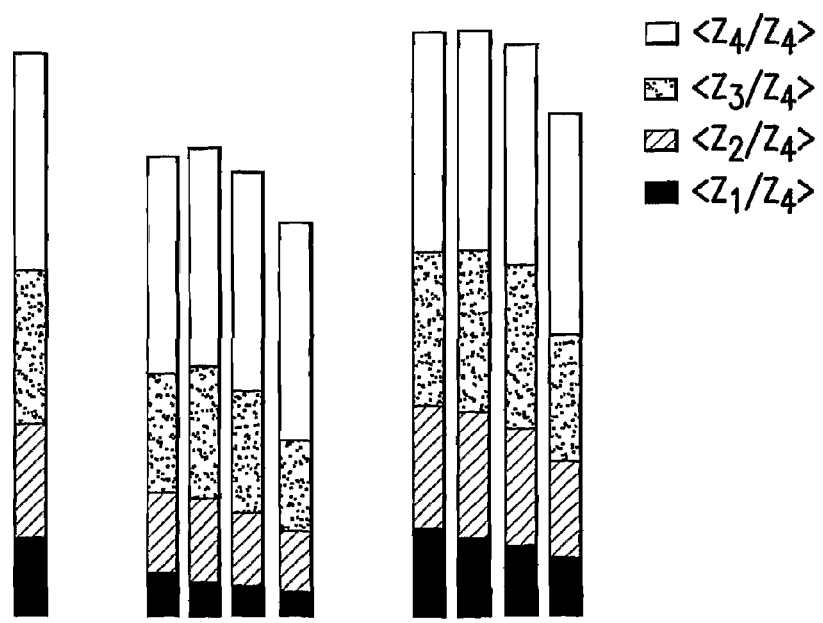
Figure 3:
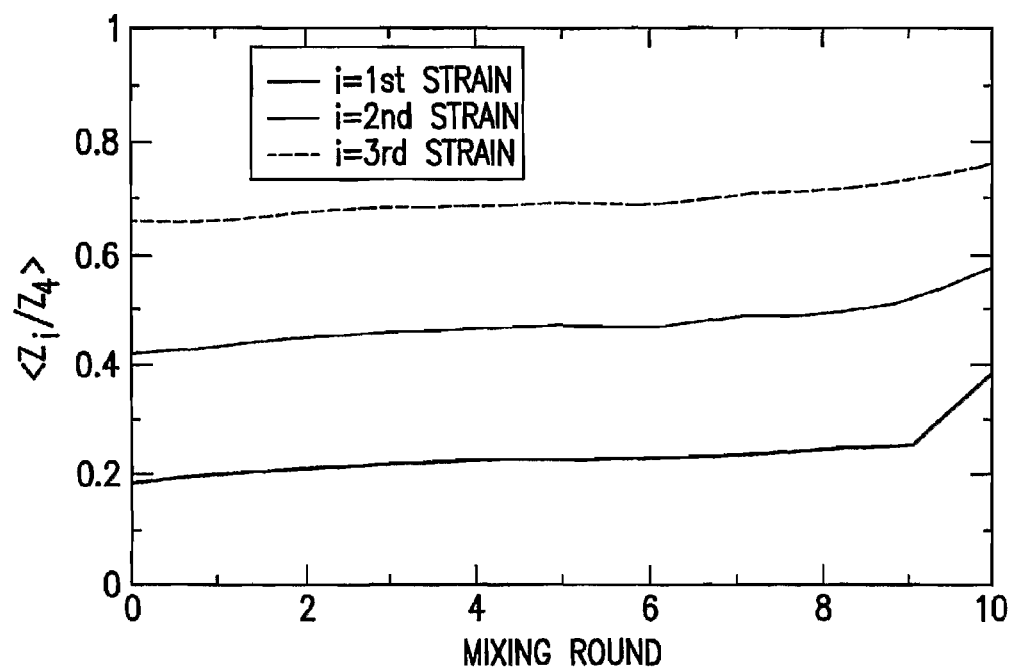
Figure 4:
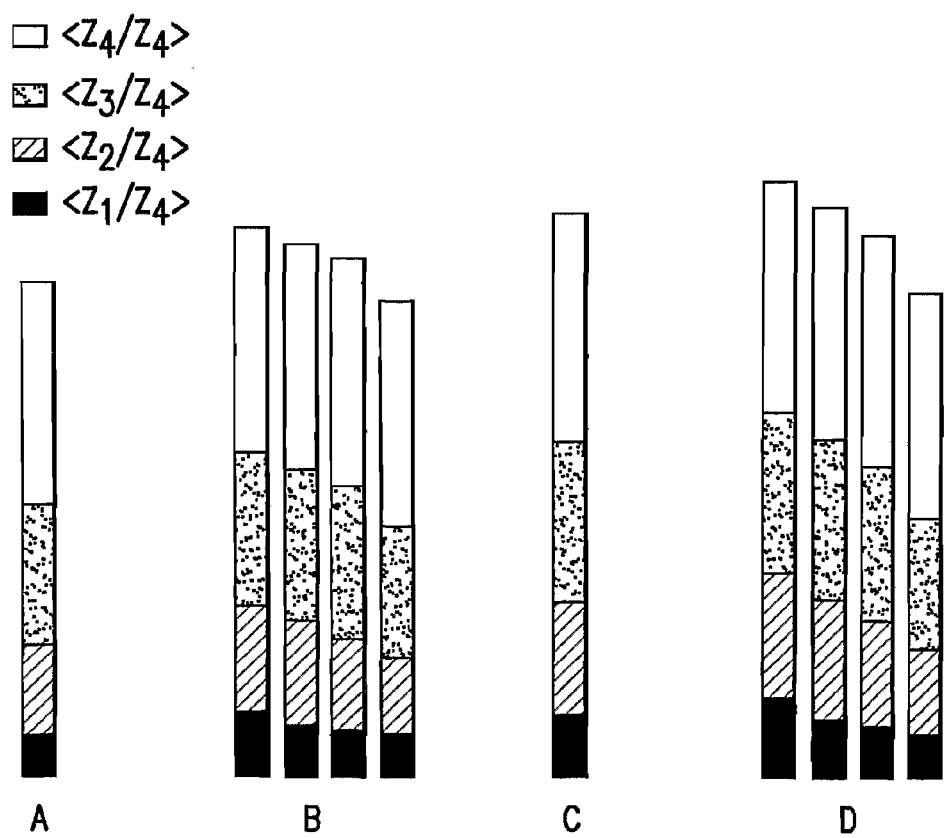
Figure 5:
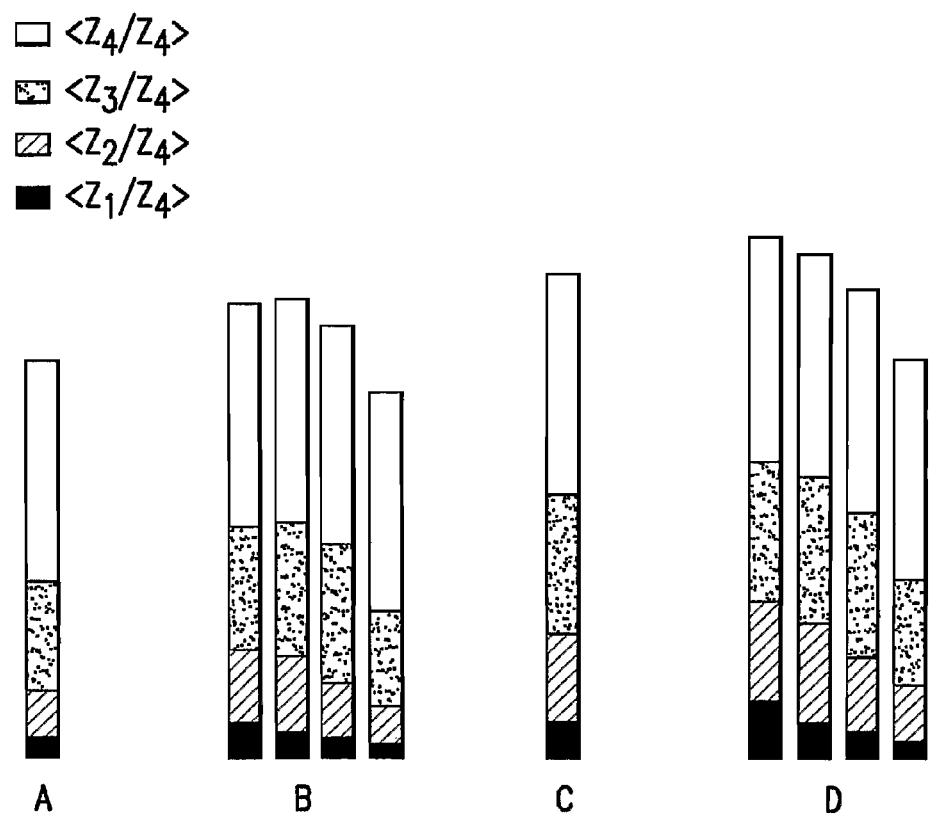
Figure 6A:
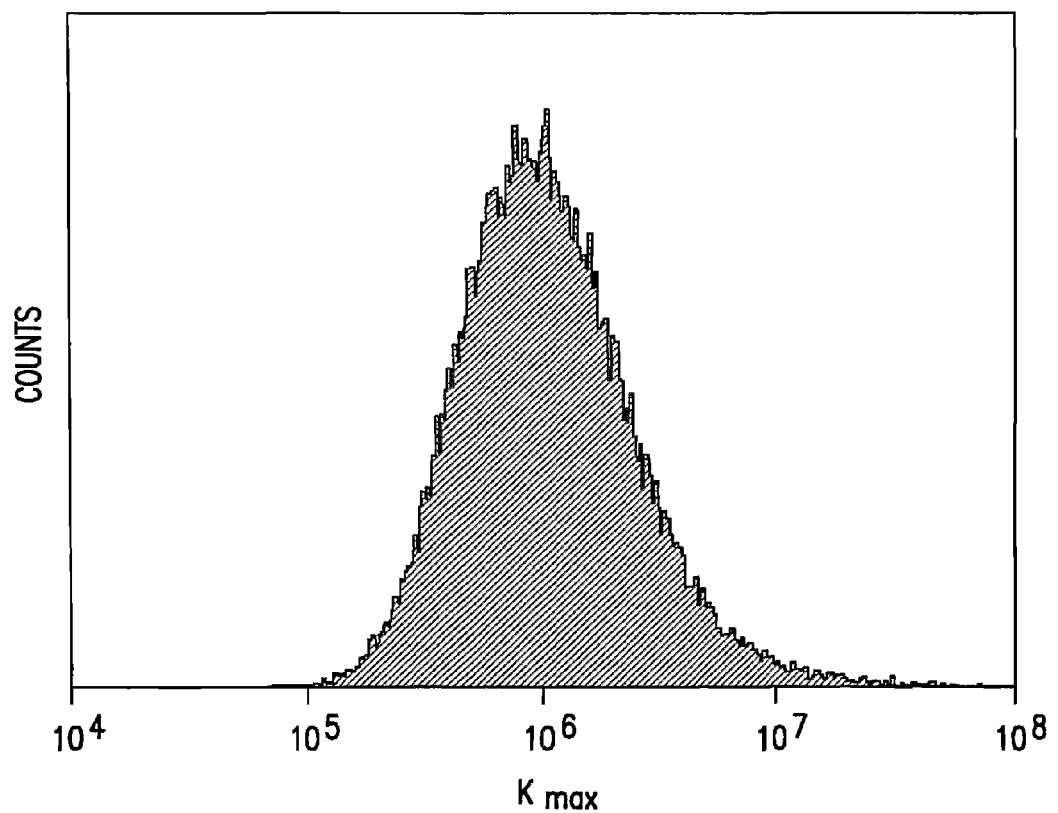
Figure 6B:
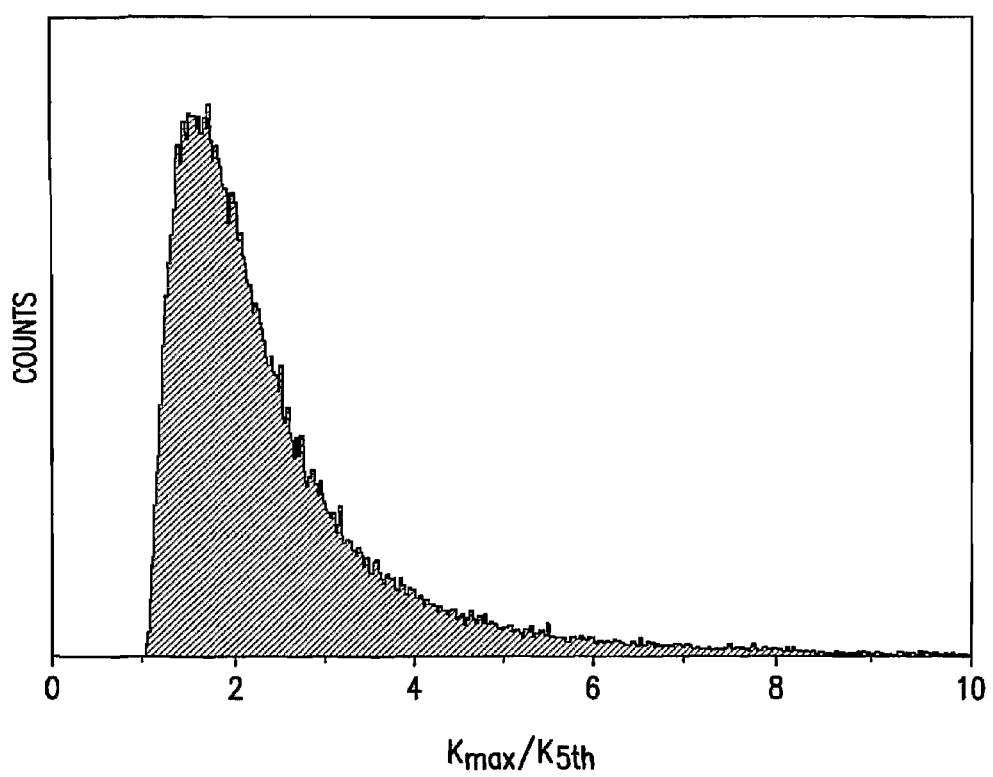

Sculpting the Immunological Response to Dengue Fever by Polytopic Vaccination The present invention is not to be limited in scope by the specific embodiments described herein. Various modifications of the invention in addition to those described herein will become apparent to those skilled in the art from the foregoing description. The following example illustrates the theoretical basis of the invention using the dengue virus. However, the methods of the present invention are believed to be generalizable to any infectious agent against which an immune response is prophylactic or therapeutic.

The twin challenges of immunodominance and heterologous immunity have hampered discovery of an effective vaccine against all four strains of dengue virus. This example provides a model that describes how T cell competition and selection impede effective vaccine design. The model's accuracy is evidenced by its ability to predict dengue vaccine clinical trial data. The model further indicates two novel methods for vaccination against dengue: polytopic injection and subdominant epitope priming.

Dengue virus infections are a serious cause of morbidity and mortality in most tropical and subtropical areas of the world (Gubler, 1998; Kurane and Takasaki, 2001; Gibbons and Vaughn, 2002). There are four strains of dengue, and immunity built up after infection by one strain of dengue virus protects only modestly or even negatively against reinfection by the other strains (Mongkolsapaya et al. 2003; Rothman, 2004; Klenerman and Zinkernagel, 1998). Thus, an effective vaccine for dengue must induce protective immunity against all four strains. To date, no such vaccine has been developed. The immunological epitopes of the four strains of the dengue virus are closely related but differ in sequence, and it is believed that the immunological response to each strain is largely to a single epitope (Mathew et al. 1996; Zivny et al. 1995). These epitope sequence differences affect the quality of the effector response. For example, simultaneous exposure to all four epitopes reduces the quality of the immune response to some of the strains, by a mechanism that is not understood. (Rothman et al. 2001; Gubler 1998). Most studies suggest that CD8+ T cell receptors (TCRs) specific for dominant epitopes suppress response to other epitopes, due to resource competition, homeostasis, apoptosis, and reduction of viral load (Yewdell and Bennink, 1999; Freitas and Rocha, 2000; Nara and Garrity, 1998).

In this example, a generalized NK, or spin glass, model of T cell original antigenic sin and immunodominance is used (Deem and Lee, 2003; Park and Deem, 2004). The model captures the stochastic nature of human immunity and realistic recognition characteristics between TCRs and virus at the sequence level. For example, the model addresses the competition of cross-active T cells to the four strains of dengue that leads to the selection of effector and memory T cells. The model is thus a simplified virtual immune system focusing on the competitive selection dynamics of CD8+ TCRs. As such, it is useful as a tool for T cell vaccine design. The results obtained with the model suggest that polytopic vaccination, that is, vaccination with a plurality of compositions, each composition being administered to a different site of the subject, wherein each composition comprises at least one antigenic molecule, wherein at least one antigenic molecule in each composition comprises one or more epitopes of the same infectious agent or a strain thereof, and wherein the one or more molecules of each composition comprise in aggregate a set of epitopes distinct from that of any other composition so administered, is efficacious for the treatment and prevention of infectious diseases, particularly diseases caused by multi-strain infectious agents.

6.1 Specific Lysis

The model captures the stochastic nature of human immunity and realistic recognition characteristics between TCRs and virus at the sequence level. Agreement within experimental error bars is observed between predictions from the model and observations from clinical vaccine trials (see FIG. 1). We emphasize that this result is not a fit, as the model was calibrated to the altered peptide lingand data (Park and Deem, 2004) before this prediction was made.

6.2 Original Antigenic Sin and Immunodominance

We first discuss how cross-immunity to the four strains of dengue shapes the T cell repertoire differently under variant immunological histories. FIG. 2*a* shows the response to a second antigen if the exposure to a first antigen exists (solid line) or not (dashed line) as a function of the difference between the first and second antigen, $p_{epitope}$. When the difference is small, the exposure to a first antigen leads to a higher clearance probability, Z, than without exposure. For a large difference, the antigen encountered in the first exposure is uncorrelated with that in the second exposure, and so immune system memory does not play a role. Interestingly, the immunological memory from the first exposure actually gives worse protection, a lower z, for intermediate differences than would no memory, which is original antigenic sin (Klenerman and Zinkernagel 1998). The epitopic variation for dengue lies in this range. During primary infection, T cell populations with higher affinity for the infecting strain are preferentially expanded and enter the memory pool. When exposure to another strain follows this first exposure, not only is the memory T cell population at a 100 to 1000 times greater concentration than the naive T cell population (Janeway et al. 2001), but also the average binding constant of the memory T cell population may initially be higher than that of the naive population, as shown by the round=0 data in FIG. 2b. For dengue, and other diseases, these memory T cells will, therefore, be selectively expanded, even though selection and expansion of the naive population would have produced superior binding constants of the effector T cells, as shown by the round=10 data in FIG. 2b. That is, memory T cells are expected to perform better against cross-active strains than would naive TCRs. But our theory shows that for dengue, from FIG. 2b, this evolved behavior of the immune system is faulted, and naive TCRs can select for superior binding affinity.

We next address how the immune response to one or two dominant strains of dengue suppresses the response to the other, subdominant strains. This immunodominance can be seen in FIG. 1. The immune response is typically strong to only a few epitopes. The immune response to these dominant epitopes suppresses the response to the other, subdominant epitopes. This immunodominance is well captured by the generalized NK theory. Even in the absence of competition of the TCRs for resources, there is immunodominance in the immune response. (FIG. 2*c*, left column). This result shows that immunodominance stems from the heterologous nature of the immune system. It appears inevitable. Vaccination with only a single strain increases the immunodominance (FIG. 2*c*, middle columns), as a result of original antigenic sin.

6.3 Sequential Dependence of Response

Priming with the subdominant epitope (FIG. 2*c*, right columns, i=1) sculpts a broader immune response and leads to reduced immunodominance in a secondary response than does priming with the dominant epitope (FIG. 2*c*, right columns, i=4). The improvement in the response against the least-recognized strain is 51%. Epidemiological studies have suggested that the order of exposure to dengue virus infections is important (Sangkawibha et al. 1984). CTLs induced by one strain may recognize another strain to a greater extent than the reverse, which increases the odds of dengue hemorrhagic fever (DHF) (Spaulding et al. 1999; Kurane and Takasaki 2001). We term this the ordering effect. FIG. 2*c* shows the effect. Our theory suggests that there is nonreciprocal CTL cross-activity among the four dengue virus strains. Initial exposure to the dominant strain will suppress the available TCRs for a subsequent exposure to a subdominant strain more quickly and harmfully than the reverse. Conversely, initial exposure to the subdominant epitope does not cause too much suppression against the dominant epitope because of the excess of high-affinity TCRs available for the dominant epitope. Our theory (FIG. 2*c*, right columns, i=1) predicts and epidemiological studies (Sangkawibha et al. 1984) show that primary exposure to the subdominant DEN-2 followed by secondary exposure to the other strains is the least likely infection sequence to produce severe dengue disease. Additionally our theory (FIG. 2*c*, right columns, i=4) predicts and epidemiological studies (Ferguson et al. 1999; Sangkawibha et al. 1984) also show that primary exposure to other strains of dengue followed by secondary exposure to the subdominant DEN-2 is the most likely infection sequence to produce severe disease (Ferguson et al. 1999; Sangkawibha et al. 1984). Our results direct that to construct and administer an optimal vaccine, the patient history and vaccine ordering effect must be considered.

6.4 Polytopic Injection

By physically separating the TCR selection process and reducing the pressure on TCR resource competition within each lymph node, the TCR repertoire can be sculpted toward the subdominant epitopes, and so there is a reduction in immunodominance. We term this the polytopic effect. FIGS. 3 and 4*c* show this effect. Immunodominance and competition through space imply that to maximize protection and minimize pathologic heterologous immunity and to achieve a long-lasting immune response, an optimal dengue vaccine should induce a high concentration of high-affinity TCRs against all four strains (Yewdell and Bennink 1999; Rothman et al. 2001; Gubler 2004; Dharakul et al. 1994). In other words, the immune system must be induced to expand TCRs against all dominant and subdominant strains. Larger values of the parameter mixing round allow for a longer period of independent TCR selection during a typical 10-round immune response period and lead to less immunodominance (FIG. 3). The parameter mixing round is relative to the T cell division time, which is typically 12-24 hours (Janeway et al. 2001). It is seen that the results are not greatly sensitive to the exact value of this lumped parameter. Some T cells may leave the lymph node before the mixing round, and some may leave after the mixing round, but the average time to leave is mixing round, and the average behavior is shown in FIG. 3. For the human immune system, the time for T cells to leave the lymph nodes plus the circulation time of the lymph system is in the range 6-10 days (Janeway et al. 2001; Fournier, 1999). Within this entire physiological range, the polytopic effect is beneficial.

6.5 Sculpting the Immunological Response to a Dengue Vaccine

By combining multi-site injection with subdominant epitope priming, a powerful vaccination protocol for sculpting the immune response to dengue is achieved (FIG. 4*d*). This new protocol is superior to multi-site injection or subdominant epitope priming alone (FIGS. 4*c* and 4*b*, respectively), both of which are superior to a traditional four-component dengue vaccine (FIG. 4*a*). Immunological memory and competition through time imply that response to a subdominant strain can be strengthened with prior exposure. Indeed, not only does patient history affect the response to vaccination, FIG. 2*a*, but also a history can be imposed by a vaccination sequence.

6.6 Discussion

Original antigenic sin and immunodominance are two sides of one coin. They both stem from the competitive selection of cross-active TCRs. Original antigenic sin acts sequentially through time and arises from competition between memory and naive T cells. Because of original antigenic sin, prior exposure history is an important factor to the immune response. Immunodominance acts simultaneously through space on T cells competing for expansion against multiple, related strains. Because of immunodominance, relatedness of strains in a multi-component vaccine is an important factor to the immune response. From FIG. 1a, we see that the competitive selection leading to original antigen sin occurs in the range $0.02 < p_{epitope} < 0.4$, in which dengue lies.

When a single strain disease begins to mutate, the two sides of the heterologous immunity coin become connected. Original antigenic sin imparts to some of the mutants a selective advantage at escaping immune system control. Concomitantly, the dominant escape mutants skew the T cell repertoire toward themselves and away from the subdominant escape mutants (Sette and Fikes 2003). These subdominant mutants can then proliferate. HIV and cancer are examples of such escape from the immune system (McMichael and Rowland-Jones 2001; Khong and Restifo 2002). In both cases, immunodominance is a significant barrier to developing effective vaccines against these multi-strain diseases.

The strategies of polytopic vaccination and subdominant epitope priming apply to vaccination against disease strains expressing multiple epitopes. In this case, the optimal strategy would be to identify and vaccination against all of the significant epitopes in each strain. While epitope based vaccines are becoming the favored approach, polytopic vaccination and subdominant epitope priming will still reduce immunodominance in whole-strain vaccines if each strain is administered separately.

The polytopic injection and subdominant epitope priming ideas apply generically to multi-strain viral diseases. Competition due to limited partial cross-activity is the reason for original antigen sin for diseases with epitopic variation in the range $0.02<p_{epitope}<0.40$. Deleterious competition is why the separate selection that occurs in multi-site injection leads to less immunodominance and why subdominant epitope priming is useful to achieve a significant number of TCRs responding to the subdominant epitopes. Our theory captures realistic recognition characteristics between the TCRs and the virus, the primary and secondary dynamics due to TCR resource competition, and the stochastic nature of heterologous human immunity. Dengue was unique in our theory because the difference between the epitopes of the four strains is roughly $p_{epitope}=0.5/9$. For strains with larger differences but which are still cross-active, as might occur with multi-strain diseases other than dengue, both subdominant epitope priming and multi-site injection continue to work effectively (FIG. 5 *a,d*). For example, vaccines against HIV (McMichael and Rowland-Jones 2001) or multi-strain cancers (Khong and Restifo 2002) should benefit from the proposed approach. When $p_{epitope}=1.0/9$, such as a variant dengue strain or other multi-strain disease, our strategies can improve recognition of the least-recognized strain by 290% improvement (FIG. 5 *a,d*) The results from our theory not only quantitatively reproduce and explain immunodominance, but also predict and explain original antigenic sin. From our theory of the ordering and multi-site effects, subdominant epitope priming followed by secondary multi-site injection of epitopes appears to be a promising vaccination strategy for dengue fever and other multi-strain diseases.

6.7 Methods

6.7.1.1 Generalized NK Model

The generalized NK model for the T-cell response considers interactions between the TCR, MHCI, and peptide epitope (Park and Deem, 2004; Deem and Lee, 2003). Parameters in the theory are shown in Table 4. The model returns the free energy of binding (U) as a function of the TCR amino acid sequence ($a_j$) and epitope amino acid sequence ($a_j^{pep}$).

TABLE 4

Parameter values for the Generalized NK model

| | Parameter | Value | Definition |
|---|---|---|---|
| TCR | $a_i$ | | Identity of amino acid at sequence position j |
| | M | 6 | Number of secondary structure subdomains |
| | N | 9 | Number of amino acids in each subdomain |
| | L | 5 | Number of subdomain types (e.g., helices, strands, loops, turns and others) |
| | $\alpha_i$ | $1 \leqq \alpha_i \leqq L$ | Type of secondary structure for the $i^{th}$ subdomain |
| | K | 4 | Local interaction range within a subdomain |
| | $\sigma_{ai}$ | | Local interaction coupling within a subdomain, for subdomain type $\alpha_i$ |
| | D | 2 | Number of interactions between subdomains |
| | $\sigma_{ij}^k$ | | Nonlocal interaction coupling between secondary structures |
| Epitope | $a_j^{pep}$ | | Identity of amino acid of epitope at sequence position j |
| | N | 9 | Number of amino acids in epitope |
| TCR-Epitope | $N_b$ | 3 | Number of hot-spot amino acids in the epitope |
| | $N_{con}$ | 3 | Number of amino acids in TCR that each hot spot interacts with |
| | $\sigma_{ij}$ | | Interaction coupling between TCR and epitope |
| | $\sigma_i^k$ | | Interaction coupling between TCR secondary structure and epitope |
| Random couplings | ω | | Gaussian random number with zero average and unit standard deviation |
| | σ | $\omega_j + \omega_i/2$ | Value of coupling for amino acid i of non-conservative type j |

The binding constant is related to the energy by $$K=e^{a-bU}$$

We determine the values of a, b in each instance of the ensemble by fixing the geometric average TCR:p-MHCI affinity to be $K=10^4$ l/mol and minimum affinity to be $K=10^2$ l/mol for the $N_{size}=10^8/10^5=1000$ distinct TCRs that respond to one epitope (Hengartner and Zinkernagel 2001; Goldrath and Bevan, 1999). This means that for the highest affinity TCR, K fluctuates between $10^5$ l/mol and $10^7$ l/mol for the different epitopes (van der Merwe and Davis 2003) (see FIG. 6).

Specific lysis is a measure of the probability that an activated T cell will recognize an antigen presenting cell that is expressing a particular peptide-MHC complex. It is given by (Park and Deem 2004)

$$L = \frac{zE/T}{1+zE/T}$$

where E/T is the effector to target ratio. The quantity z is, therefore, the average clearance probability of one TCR:

$$z = 1/N_{size} \sum_{i=1}^{N_{size}} \min(1, K^i/10^6).$$

6.7.1.2 TCR Selection Dynamics

Figure 7:
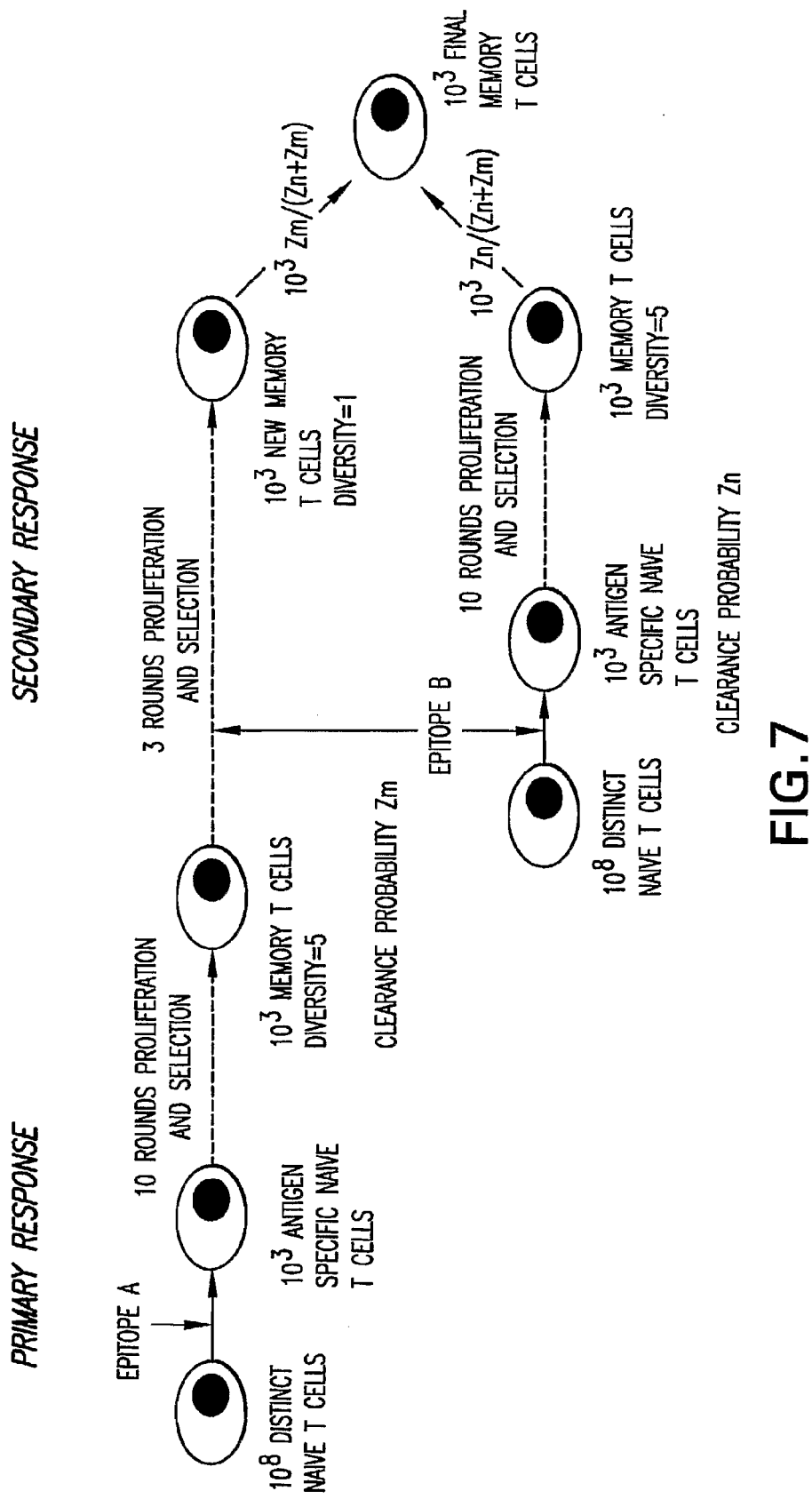

The naive TCR repertoire is generated randomly from gene fragments. This is accomplished by constructing the TCRs from subdomain pools. Fragments for each of the L subdomain types are chosen randomly from 13 of the 100 lowest energy subdomain sequences. This diversity mimics the known TCR diversity, $(13 \times L)^M \cong 10^{11}$ (Kesmir, Borghans, and de Boer, 2000). Only 1 in $10^5$ naive TCRs responds to any particular antigen, and there are only $10^8$ distinct TCRs present at any one point in time in the human immune system (Zinkernagel and Hengartner 2001; Goldrath and Bevan 1999), so the primary response starts with a repertoire of $N_{size}=10^3$ distinct TCRs. A flow diagram of the TCR selection dynamics is shown in FIG. 7.

The T-cell-mediated response is driven by cycles of concentration expansion and selection for better binding constants. The primary response increases the concentration of selected TCRs by 1000 fold over 10 rounds, with a rough T cell doubling time of 12-24 hours. The diversity of the memory sequences is 0.5% of that of the naive repertoire (Arstila et al. 1999). Specifically, 10 rounds of selection are performed during the primary response, with the top x=58% of the sequences chosen at each round. The T cell division may occur more rapidly than once per day, and the mixing round parameter is measured in the time scale of T cell divisions. This procedure mimics the concentration expansion factor of $10^3 \cong 2^{10}$ in the primary response and leads to 0.5% diversity of the memory repertoire, because $0.58^{10} \cong 0.5\%$ and 10 rounds of doubling leads to a concentration expansion of $2^{10}=10^3$.

6.7.1.3 Parameters for Dengue

For each epitope, the sequence, model, and VDJ selection pools differ by $p_{epitope}$ (Deem and Lee, 2003), where $p_{epitope}=$(non-conservative+0.5*conservative)amino acid differences in epitope divided by the total number of amino acids in epitope.

To generate results, an average over many instances of these random epitope sequences, models, and VDJ selection pools that differ by $p_{epitope}$ is taken. In other words, the different strains of dengue were chosen so that they differ by the requisite $p_{epitope}$. To compute average results, four new random epitopes were generated each time. The initial TCR repertoire is redetermined for each realization of the model—this must be done because the $U^{sd}$ that defines the TCR repertoire is different in each instance of the ensemble.

For dengue, the nonstructural (NS3) protein is an attractive candidate for a subunit vaccine (Mathew et al. 1996). We consider the observed single conservative amino acid change in the epitope (Zivny et al. 1995), and so $p_{epitope}=0.5/9$. Qualitatively similar results are obtained for $p_{epitope}=1/9$, as might occur for drift strains of dengue. We assume that for each strain of dengue, only a single epitope is recognized by the immune system.

6.7.1.4 Polytopic Vaccination

For a polytopic vaccination, the different strains are injected in different physical locations and evoke an immune response that evolves independently in different lymph nodes until mixing round, after which the lymph system is well-mixed. This is modeled by performing a response against each of the four strains independently, with selection among $10^3$ TCRs for each strain, until mixing round. At mixing round, $10^3$ TCRs are randomly chosen from the $4\times10^3$ partially evolved TCRs. These $10^3$ TCRs are then evolved from mixing day until round 10. In this way, we model the independent response in different lymph nodes against each strain that occurs early on and the combined response in a typical lymph node against all strains that occurs after the lymph system has mixed.

6.8 References

Arstila, T. P., Casrouge, A., Baron, V., Even, J., Kanellopoulos, J., and Kourilsky, P. (1999). Direct estimate of the human T cell receptor diversity. Science 286, 958-961.

Cole, G. A., Hogg, T. L., Coppola, M. A., and Woodland, D. L. (1997). Efficient priming of CD8+ memory T cells specific for a subdominant epitope following Sendai virus infection. J. Immunol. 158, 4301-4309.

Deem, M. W. and Lee, H. Y. (2003). Sequence space localization in the immune system response to vaccination and disease. Phys. Rev. Lett. 91, 068101-1-068101-4.

Dharakul, T., Kurane, I., Bhamarapravati, N., Yoksan, S., Vaughn, D. W., Hoke, C. H., and Ennis, F. A. (1994). Dengue virus-specific memory T cell responses in human volunteers receiving a live attenuated dengue virus type 2 candidate vaccine. J. Infect. Dis. 170(1), 27-33.

Ferguson, N., Anderson, R., and Gupta, S. (1999). The effect of antibody-dependent enhancement on the transmission dynamics and persistence of multiple-strain pathogens. Proc. Natl. Acad. Sci. USA 96, 790-794.

Fournier, R. L. (1999). Basic Transport Phenomena in Biomedical Engineering (Philadelphia: Taylor & Francis).

Freitas, A. A. and Rocha, B. (2000). Population biology of lymphocytes: The flight for survival. Annu. Rev. Immunol. 18, 83-111.

Gibbons, R. V. and Vaughn, D. W. (2002). Dengue: An escalating problem. BMJ. 324, 1563-1566.

Goldrath, A. W. and Bevan, M. J. (1999). Selecting and maintaining a diverse T-cell repertoire. Nature 402, 255-262.

Gubler, D. J. (1998). Dengue and dengue hemorrhagic fever. Clin. Microbiol. Rev. 11(3), 480-496.

Gubler, D. J. (2004). Cities spawn epidemic dengue viruses. Nature Medicine 10, 129-130.

Hengartner, H. and Zinkernagel, R. M. (2001). Regulation of the immune response by antigen. Science 120, 251-253.

Hon, H. and Jacob, J. (2004). Tracking dendritic cells in vivo: Insights into DC biology and function. Immunologic Res. 29, 69-80.

Janeway, C. A., Travers, P., Walport, M., and Shlomchik, M. (2001). Immunobiology: The Immune System in Health and Disease (New York: Garland science publishing), 5th edn.

Kesmir, C., Borghans, J. A. M., and de Boer, R. J. (2000). Diversity of human T cell receptors. Science 288, 1135.

Khong, H. T. and Restifo, N. P. (2002). Natural selection of tumor variants in the generation of "tumor escape" phenotypes. Nature Immunol. 3, 999-1005.

Klenerman, P. and Zinkernagel, R. M. (1998). Original antigenic sin impairs cytotoxic T lymphocyte responses to viruses bearing variant epitopes. Nature 394, 482-485.

Kurane, I. and Takasaki, T. (2001). Dengue fever and dengue haemorrhagic fever: Challenges of controlling an enemy still at large. Rev. Med. Virol. 11, 301-311.

Makki, A., Weidt, G., Blachere, N. E., Lefrancois, L., and Srivastava, P. K. (2002). Immunization against a dominant tumor antigen abrogates immunogenicity of the tumor. Cancer Immunity 2, 4.

Martin-Fontecha, A., Sebastiani, S., Hopken, U. E., Uguccioni, M., Lipp, M., A, A. L., and Sallusto, F. (2003). Regulation of dendritic cell migration to the draining lymph node: Impact on T lymphocyte traffic and priming. J. Exp. Med. 198, 615-621.

Mathew, A., Kurane, I., Rothman, A. L., Zeng, L. L., Brinton, M. A., and Ennis, F. A. (1996). Dominant recognition by human CD8+ cytotoxic T lymphocytes of dengue virus nonstructural proteins NS3 and NS1.2a. J. Clin. Invest. 98, 1684-1692.

McMichael, A. J. and Rowland-Jones, S. L. (2001). Cellular immune responses to HIV. Nature 410, 980-987.

Mongkolsapaya, J., Dejnirattisai, W., Xu, X., Vasanawathana, S., Tangthawornchaikul, N., Chairunsri, A., Sawasdivorn, S., Duangchinda, T., Dong, T., Rowland-Jones, S., Yenchitsomanus, P., McMichael, A., Malasit, P., and Screaton, G. (2003). Original antigenic sin and apoptosis in the pathogenesis of dengue hemorrhagic fever. Nature Medicine 9, 921-927.

Nara, P. L. and Garrity, R. (1998). Deceptive imprinting: a cosmopolitan strategy for complicating vaccination. Vaccine 16(19), 1780-1787.

Park, J. M. and Deem, M. W. (2004). Correlations in the T cell response to altered peptide ligands. Physica A. 341, 455-470.

Rothman, A. L. (2004). Dengue: Defining protective versus pathologic immunity. J. Clin. Invest. 113, 946-951.

Rothman, A. L., Kanesa-thasan, N., West, K., Janus, J., Saluzzo, J. F., and Ennis, F. A. (2001). Induction of T lymphocyte responses to dengue virus by a candidate tetravalent live attenuated dengue virus vaccine. Vaccine 19, 4694-4699.

Sangkawibha, N., Rojanasuphot, S., Ahandrik, S., Viriyapongse, S., Jatanasen, S., Salitul, V., Phanthumachinda, B., and Halstead, S. B. (1984). Risk factors in dengue shock syndrome: A prospective epidemiologic study in Rayong, Thailand. I. The 1980 outbreak. Am. J. Epidemiol. 120, 653-669.

Schreiber, H., Wu, T. H., Nachman, J., and Kast, W. M. (2002). Immunodominance and tumor escape. Semin. Cancer. Biol. 12(1), 25-31.

Sette, A. and Fikes, J. (2003). Epitope-based vaccines: An update on epitope identification, vaccine design and delivery. Curr. Opin. Immunol. 15, 461-470.

Spaulding, A. C., Kurane, I., Ennis, F. A., and Rothman, A. L. (1999). Analysis of murine CD8+ T-cell clones specific for the dengue virus NS3 protein: Flavivirus cross-reactivity and influence of infecting serotype. J. Virol. 73, 398-403.

van der Merwe, P. A. and Davis, S. J. (2003). Molecular interactions mediating T cell antigen recognition. Annu. Rev. Immunol. 21, 659-684.

van der Most, R. G., Sette, A., Oseroff, C., Alexander, J., Murali-Krishna, K., Lau, L., Southwood, S., Sidney, J., Chesnut, R. W., Matloubian, M., and Ahmed, R. (1996). Analysis of cytotoxic T cell responses to dominant and subdominant epitopes during acute and chronic lymphocytic choriomeningitis virus infection. J. Immunol. 157, 5543-5554.

Yewdell, J. W. and Bennink, J. R. (1999). Immunodominance in major histocompatibility complex class I-restricted T lymphocyte responses. Annu. Rev. Immunol. 17, 51-88.

Zinkernagel, R. M. and Hengartner, H. (2001). Regulation of the immune response by antigen. Science 293, 251-253.

Zivny, J., Kurane, I., Leporati, A. M., Ibe, M., Takiguchi, M., Zeng, L. L., Brinton, M. A., and Ennis, F. A. (1995). A single nine-amino acid peptide induces virus-specific, CD8+ human cytotoxic T lymphocyte clones of heterogeneous serotype specificities. J. Exp. ed. 182, 853-863.

7. EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method of modulating the immune response to one or more viruses in a subject in need thereof comprising administering to the subject a plurality of compositions in amounts effective to modulate said immune response, each composition being administered to a different site of the subject wherein each composition comprises at least one purified antigenic molecule, wherein at least one purified antigenic molecule in each composition comprises a set of one or more epitopes of one or more viral strains, and wherein the one or more purified antigenic molecules of each composition comprise in aggregate a set of epitopes distinct from that of any other composition so administered, wherein the distance between each pair of sites is greater than the distance between any two anatomically distinct lymph nodes or groups of lymph nodes nearest each site and wherein the distinct epitopes between the compositions differ from each other by an epitopic variance defined as the sum of the number of non-conservative amino acid changes and one half of the number of conservative amino acid changes divided by the total number of amino acids in the epitope, and wherein the epitopic variance between the distinct epitopes between the compositions is between 0.05-0.5.

2. The method of claim 1, wherein at least two compositions do not comprise epitopes of the same viral strain.

3. The method of claim 1, wherein no two compositions comprise the same epitopes.

4. The method of claim 1, wherein each composition comprises at least one purified antigenic molecule comprising one or more subdominant epitopes of one or more viruses.

5. The method of claim 1, wherein each composition comprises at least one purified antigenic molecule comprising one or more dominant epitopes of one or more viruses.

6. The method of claim 1, wherein each antigenic molecule is a peptide which consists of an amino acid sequence 25 amino acids or less.

7. The method of claim 6, wherein the amino acid sequence of each said peptide consists of 12 amino acids or less.

8. The method of claim 7, wherein the amino acid sequence of each said peptide consists of 9 amino acids.

9. The method of claim 6, wherein the epitopes are epitopes for different major histocompatibility complex ("MHC") alleles.

10. The method of claim 9, wherein the epitopes are overlapping epitopes for different major histocompatibility complex ("MHC") alleles.

11. The method of claim 1, wherein the plurality of compositions is two to ten compositions.

12. The method of claim 1, wherein the virus is selected from the group consisting of a lymphocytic choriomeningitis virus, a hepatitis B virus, an Epstein Barr-virus, an influenza virus, and a human immunodeficiency virus.

13. The method of claim 1, wherein the virus is a member of the Flaviviridae family of viruses.

14. The method of claim 13, wherein the flavivirus is selected from the group consisting of dengue, Kunjin, Japanese encephalitits, West Nile, and yellow fever virus.

15. The method of claim 14, wherein the virus is a dengue virus.

16. The method of claim 1, wherein the plurality of compositions is two to four compositions.

17. The method of claim 16, wherein the plurality of compositions is two to three compositions.

18. A method of modulating the immune response to one or more viruses in a subject in need thereof comprising administering to the subject a plurality of compositions in amounts effective to modulate said immune response, each composition being administered to a different site of the subject wherein each composition comprises at least one purified antigenic molecule, wherein at least one purified antigenic molecule in each composition comprises a set of one or more epitopes of one or more viral strains, and wherein the one or more purified antigenic molecules of each composition comprise in aggregate a set of epitopes distinct from that of any other composition so administered, wherein the distance between each pair of sites is greater than the distance between any two anatomically distinct lymph nodes or groups of lymph nodes nearest each site and wherein the distinct epitopes between the compositions differ from each other by an epitopic variance defined as the sum of the number of non-conservative amino acid changes and one half of the number of conservative amino acid changes divided by the total number of amino acids in the epitope, and wherein the epitopic variance between the distinct epitopes between the compositions is between 0.02-0.4.

19. A kit comprising in separate containers at least two compositions, each composition comprising at least one antigenic molecule, wherein at least one antigenic molecule in each composition comprises one or more epitopes of the same infectious agent or strain thereof and wherein the one or more molecules of each composition comprise in aggregate a set of epitopes distinct from that of said other composition or compositions, wherein the distinct epitopes between the compositions differ from each other by an epitopic variance defined as the sum of the number of non-conservative amino acid changes and one half of the number of conservative amino acid changes divided by the total number of amino acids in the epitope, and wherein the epitopic variance between the distinct epitopes between the compositions is between 0.05-0.5 and instructions for administering each composition to a separate site of a subject.

20. The kit of claim 19, comprising in separate containers at least four compositions.

21. The kit of claim 19, comprising in separate containers at least three compositions.

22. A kit comprising in separate containers at least two compositions, each composition comprising at least one antigenic molecule, wherein at least one antigenic molecule in each composition comprises one or more epitopes of the same infectious agent or strain thereof and wherein the one or more molecules of each composition comprise in aggregate a set of epitopes distinct from that of said other composition or compositions, wherein the distinct epitopes between the compositions differ from each other by an epitopic variance defined as the sum of the number of non-conservative amino acid changes and one half of the number of conservative amino acid changes divided by the total number of amino acids in the epitope, and wherein the epitopic variance between the distinct epitopes between the compositions is between 0.02-0.4 and instructions for administering each composition to a separate site of a subject.

* * * * *

UNITED STATES PATENT AND TRADEMARK OFFICE
CERTIFICATE OF CORRECTION

| | | |
|---|---|---|
| PATENT NO. | : 8,110,196 B2 | Page 1 of 1 |
| APPLICATION NO. | : 11/118917 | |
| DATED | : February 7, 2012 | |
| INVENTOR(S) | : Michael Deem et al. | |

It is certified that error appears in the above-identified patent and that said Letters Patent is hereby corrected as shown below:

ON THE TITLE PAGE:

Item (73) Assignee: replace "Polytopas LLC" with --Polytopos LLC--

Signed and Sealed this
Twentieth Day of March, 2012

David J. Kappos
*Director of the United States Patent and Trademark Office*